(12) United States Patent
Cox, III

(10) Patent No.: US 8,748,392 B2
(45) Date of Patent: Jun. 10, 2014

(54) METHODS OF TREATMENT USING CYSTEINE VARIANTS OF INTERLEUKIN-11

(75) Inventor: George N. Cox, III, Louisville, CO (US)

(73) Assignee: Bolder BioTechnology Inc., Boulder, CO (US)

( * ) Notice: Subject to any disclaimer, the term of this patent is extended or adjusted under 35 U.S.C. 154(b) by 151 days.

(21) Appl. No.: 13/365,158

(22) Filed: Feb. 2, 2012

(65) Prior Publication Data

US 2012/0231040 A1 Sep. 13, 2012

Related U.S. Application Data

(63) Continuation of application No. 12/391,896, filed on Feb. 24, 2009, now Pat. No. 8,133,480, which is a continuation of application No. 11/544,473, filed on Oct. 5, 2006, now Pat. No. 7,495,087, which is a continuation-in-part of application No. 10/298,148, filed on Nov. 15, 2002, now Pat. No. 7,153,943, which is a continuation-in-part of application No. 09/462,941, filed as application No. PCT/US98/14497 on Jul. 13, 1998, now Pat. No. 6,608,183.

(60) Provisional application No. 60/724,204, filed on Oct. 5, 2005, provisional application No. 60/332,285, filed on Nov. 15, 2001, provisional application No. 60/418,040, filed on Oct. 11, 2002, provisional application No. 60/052,516, filed on Jul. 14, 1997.

(51) Int. Cl.
*C07K 14/52* (2006.01)
*A61K 38/20* (2006.01)

(52) U.S. Cl.
USPC ......... 514/21.2; 424/85.2; 530/351; 530/402; 435/69.52

(58) Field of Classification Search
None
See application file for complete search history.

(56) References Cited

U.S. PATENT DOCUMENTS

| | | | |
|---|---|---|---|
| 4,588,585 A | 5/1986 | Mark et al. |
| 4,636,463 A | 1/1987 | Altman et al. |
| 4,678,751 A | 7/1987 | Goeddel |
| 4,855,238 A | 8/1989 | Gray et al. |
| 4,921,699 A | 5/1990 | DeChiara et al. |
| 5,166,322 A | 11/1992 | Shaw et al. |
| 5,206,344 A | 4/1993 | Katre et al. |
| 5,208,158 A | 5/1993 | Bech et al. |
| 5,382,657 A | 1/1995 | Karasiewicz et al. |
| 5,710,027 A | 1/1998 | Hauptmann et al. |
| 5,766,897 A | 6/1998 | Braxton |
| 5,849,535 A | 12/1998 | Cunningham et al. |
| 6,171,824 B1 | 1/2001 | Todaro et al. |
| 6,608,183 B1 | 8/2003 | Cox, III |
| 6,753,165 B1 | 6/2004 | Cox et al. |
| 6,809,178 B2 | 10/2004 | Evans et al. |
| 7,148,333 B2 | 12/2006 | Cox, III |
| 7,153,943 B2 | 12/2006 | Cox, III et al. |
| 7,214,779 B2 | 5/2007 | Cox, III |
| 7,232,885 B2 | 6/2007 | Cox, III |
| 7,253,267 B2 | 8/2007 | Cox, III |
| 7,270,809 B2 | 9/2007 | Cox, III |
| 7,306,931 B2 | 12/2007 | Rosendahl et al. |
| 7,309,781 B2 | 12/2007 | Cox, III |
| 7,314,921 B2 | 1/2008 | Cox, III |
| 7,345,149 B2 | 3/2008 | Cox, III |
| 7,345,154 B2 | 3/2008 | Cox, III |
| 7,399,839 B2 | 7/2008 | Cox et al. |
| 7,495,087 B2 | 2/2009 | Cox, III |
| 7,560,101 B2 | 7/2009 | Cox, III |
| 7,629,314 B2 | 12/2009 | Cox, III |
| 7,732,572 B2 | 6/2010 | Cox, III |
| 7,795,396 B2 | 9/2010 | Cox, III |
| 7,824,669 B2 | 11/2010 | Cox et al. |
| 7,947,655 B2 | 5/2011 | Cox, III et al. |
| 7,959,909 B2 | 6/2011 | Cox |
| 7,964,184 B2 | 6/2011 | Cox |
| 7,994,124 B2 | 8/2011 | Cox |
| 8,133,480 B2 | 3/2012 | Cox |
| 2003/0166865 A1 | 9/2003 | Cox, III |
| 2008/0076706 A1 | 3/2008 | Cox |
| 2009/0060863 A1 | 3/2009 | Cox |
| 2009/0269804 A1 | 10/2009 | Rosendahl et al. |
| 2011/0172151 A1 | 7/2011 | Cox, III et al. |
| 2011/0250169 A1 | 10/2011 | Cox, III |
| 2012/0064573 A1 | 3/2012 | Cox, III |

FOREIGN PATENT DOCUMENTS

| | | |
|---|---|---|
| CA | 2066370 | 4/1996 |
| EP | 0243153 | 10/1987 |
| EP | 0355460 | 2/1990 |
| EP | 0458064 | 11/1991 |
| JP | 02-234692 | 9/1990 |
| JP | 04-164098 | 9/1992 |
| JP | 04-507099 | 12/1992 |
| JP | 5-268983 | 10/1993 |
| JP | 6-510904 | 12/1994 |
| JP | 9-503396 | 4/1997 |
| JP | 10-507080 | 7/1998 |

(Continued)

OTHER PUBLICATIONS

Alberts et al., "The birth, assembly and death of proteins," Chapter 5 in Molecular Biology of the Cell, Third Edition, Garland Publishing, Inc. New York, NY, 1994, ISBN 0-8153-1619-4, pp. 212-216.

Barton et al., "Identification of Three Distinct Receptor Binding Sites of Murine Interleukin-11," The Journal of Biological Chemistry, Feb. 1999, vol. 274(9), pp. 5755-5761.

Bazan et al., "Unraveling the Structure of IL-2," Science, Jul. 1992, vol. 257(5068), pp. 410-413.

(Continued)

*Primary Examiner* — Elly-Gerald Stoica
(74) *Attorney, Agent, or Firm* — Sheridan Ross P.C.

(57) ABSTRACT

Disclosed are cysteine variants of interleukin-11 (IL-11) and methods of making and using such proteins in therapeutic applications.

7 Claims, No Drawings

(56) References Cited

FOREIGN PATENT DOCUMENTS

| | | |
|---|---|---|
| JP | 04-504801 | 2/2004 |
| WO | WO 87/01132 | 2/1987 |
| WO | WO 89/10964 | 11/1989 |
| WO | WO 90/12874 | 11/1990 |
| WO | WO 90/13310 | 11/1990 |
| WO | WO 93/00109 | 1/1993 |
| WO | WO 93/06217 | 4/1993 |
| WO | WO 94/12219 | 6/1994 |
| WO | WO 94/12638 | 6/1994 |
| WO | WO 94/12639 | 6/1994 |
| WO | WO 94/22466 | 10/1994 |
| WO | WO 95/11987 | 5/1995 |
| WO | WO 95/32003 | 11/1995 |
| WO | WO 95/034326 | 12/1995 |
| WO | WO 96/04385 | 2/1996 |
| WO | WO 96/11949 | 4/1996 |
| WO | WO 96/31537 | 10/1996 |
| WO | WO 96/36362 | 11/1996 |
| WO | WO 97/11370 | 3/1997 |
| WO | WO 97/41887 | 11/1997 |
| WO | WO 98/25971 | 6/1998 |
| WO | WO 98/37200 | 8/1998 |

OTHER PUBLICATIONS

Bazan, "Haemopoietic receptors and helical cytokines," Immunology Today, 1990, vol. 11, pp. 350-354.

Benhar et al. "Pseudomonas exotoxin A mutants. Replacement of surface-exposed residues in domain III with cysteine residues that can be modified with polyethylene glycol in a site-specific manner." Journal of Biological Chemistry, May 1994, vol. 269, No. 18, pp. 13398-13404.

Bowie et al., "Deciphering the Message in Protein Sequences: Tolerance to Amino Acid Substitutions," Science, Mar. 1999, vol. 247(4948), pp. 1306-1310.

Campbell et al., "Pegylated peptides: V. Carboxy-terminal PEGylated analogs of growth hormone-releasing factor (GRF) display enhanced duration of biological activity in vivo," J Peptide Res, Jun. 1997, vol. 49, pp. 527-537.

Caron et al., "Engineered humanized dimeric forms of IgG are more effective antibodies," J Exp Med, Oct. 1992, vol. 176(4), pp. 1191-1195.

Chang et al., "High level of secretion of human growth hormone by E. Coli," Gene, 1987, vol. 55, pp. 189-196.

Cosenza et al., "Disulfide Bond Assignment in Human Interleukin-7 by Matrix-assisted Laser Desorption/Ionization Mass Spectroscopy and Site-directed Cysteine to Serine Mutational Analysis," The Journal of Biological Chemistry, Dec. 26, 1997, vol. 272(52), pp. 32995-33000.

Cunningham et al., "High-Resolution Epitope Mapping of hGH-Receptor Interactions by Alanine-Scanning Mutagenesis," Science, 1989, vol. 244, pp. 1081-1085.

Cunningham et al., "Receptor and Antibody Epitopes in Human Growth Hormone Identified by Homolog-Scanning Mutagenesis," Science, 1989, vol. 243, pp. 1330-1336.

Czupryn et al., "Alanine-scanning Mutagenesis of Human Interleukin-11: Identification of Regions Important for Biological Activity," Annals of the New York Academy of Sciences, Jul. 1995, vol. 762, pp. 152-164.

Czupryn et al., "Structure-Function Relationships in Human Interleukin-11," Journal of Biological Chemistry, Jan. 1995, vol. 270(2), pp. 978-985.

DeVos et al., "Human Growth Hormone and Extracellular Domain of Its Receptor: Crystal Structure of the Complex," Science, vol. 255, Jan. 17, 1992, pp. 306-312.

Edge et al., "Interferon Analogues from Synthetic Genes: An Approach to Protein Structure-Activity Studies," Interferon, 1986, vol. 7, pp. 1-46.

Evinger et al., "Recombinant Human Leukocyte Interferon Produced in Bacteria Has Antiproliferative Activity," J. Biol. Chem., 1981, vol. 256(5), pp. 2113-2114.

Goodson et al., "Site-Directeed Pegylation of Recombinant Interleukin-2 at its Glycosylation Site," Bio/Technology, 1990, vol. 8, pp. 343-346.

Harmegnies et al., "Characterization of a potent human interleukin-11 agonist," Biochemical Journal, 2003, vol. 375, pp. 23-32.

Hsiung et al., "High level of expression, efficient ad folding of human growth hormone E. Coli," Bio/Technology, 1986, vol. 4, pp. 991-995.

Ishikawa et al., "The Substitution of Cysteine 17 of Recombinant Human G-CSF with Alanine Greatly Enhanced its Stability," Cell Structure and Function, 1992, vol. 17(1), pp. 61-65.

Karpusas et al., "The crystal structure of human interferon β at 2.2-Å resolution," Proc. Natl. Acad. Sci. USA, 1997, vol. 94, pp. 11813-11818.

Kawashima et al., "Molecular cloning of cDNA encoding adipogenesis inhibitory factor and identity with interleukin-11," FEBS Letters, Jun. 1991, vol. 283(2), pp. 199-202.

Kinstler et al. "Mono-N-terminal poly(ethylene glycol)-protein conjugates," Advanced Drug Delivery Reviews, Jun. 2002, vol. 54, No. 4, pp. 477-485.

Kroemer et al., "Prediction of three-dimensional structure of IL-7 by homology modeling," Protein Engineering, 1996, vol. 9, pp. 493-498.

Kuan et al. "Pseudomonas exotoxin A mutants. Replacement of surface exposed residues in domain II with cysteine residues that can be modified with polyethylene glycol in a site-specific manner." Journal of Biological Chemistry, Mar. 1994, vol. 269, No. 10, pp. 7610-7616.

Lowman and Wells, "Affinity Maturation of Human Growth Hormone by Monovalent Phage Display," J. Mol. Biol., 1993, vol. 234, pp. 564-578.

Lydon et al., "Immunochemical Mapping of α-2 Interferon," Biochemistry, 1985, vol. 24, pp. 4131-4141.

Miyadi et al., "Importance of the Carboxy-terminus of Human Interleukin-11 in Conserving Its Biological Activity," Bioscience, biotechnology, and biochemistry, Mar. 1996, vol. 60(3), pp. 541-542.

Mott and Campbell, "Four-helix bundle growth factors and their receptors: protein-protein interactions," Curr Opin Struct Biol, 1995, vol. 5, pp. 114-121.

Olins et al., "Saturation muatgenesis of human interleukin-3," Journal of Biological Chemistry, Oct. 1995, vol. 270(40), pp. 23754-23760.

Paul et al., "Molecular cloning of a cDNA encoding interleukin 11, a stromal cell-derived lymphonpoietic and hematopoietic cytokine," Proceedings of the National Academy of Sciences, USA, Oct. 1990, vol. 87(19), pp. 7512-7516.

Quelle et al., "Phosphorylatable and epitope-tagged human erythropoietins: utility and purification of native baculovirus-derived forms," Protein Expr Purif, Dec. 1992, vol. 3(6), pp. 461-469.

Senda et al., "Refined crystal structure of recombinant murine interferon-beta at 2.15 A resolution," J. Mol. Biol., 1995, vol. 253, pp. 187-207.

Sprang et al., "Cytokine structural taxonomy and mechanisms of receptor engagement," Curr. Opin. Struct. Biol., 1993, vol. 3, pp. 815-827.

Tacken et al., "Definition of receptor binding sites on human interleukin-11 by molecular modeling-guided mutagenesis," European Journal of Biochemistry, Oct. 1999, vol. 265(2), pp. 645-655.

Takahashi et al., "Short stature caused by a mutant growth hormone with an antagonistic effect," Endocr J., Oct. 1996, vol. 43, Suppl:S27-32.

Tang et al., "Studies on the PEGylation of Protein at a Specific Site: Sulfhydryl-PEGylation of 97Cys-IFN-gamma," Sheng Wu Hua Xue Yu Sheng Wu Wu Li Xue Bao (Shanghai), 1996, vol. 28(3), pp. 312-315 (Abstract only).

Tiebel et al., "Conformational changes necessary for gene regulation by Tet repressor assayed by reversible disulfide bond formation," The EMBO Journal, Sep. 1998, vol. 17(17), pp. 5112-5119.

Valenzuela et al., "Is Sequence Conservation in Interferons Due to Selection for Functional Proteins," Nature, Feb. 1985, vol. 313(21), pp. 698-700.

Walter et al., "Crystal structure of a complex between interferon-gamma and its soluble high-affinity receptor," Nature, 2000, vol. 376, pp. 230-235.

(56) References Cited

OTHER PUBLICATIONS

Wang et al., "Engineering and use of (32)P-labeled human recombinant interleukin-11 for receptor binding studies," Eur. J. Biochem., 2002, vol. 269, pp. 61-68.

Watson, Molecular Biology of the gene, Third Edition, Benjamin, eds., 1977, IISBN 0-8053-9609-8, p. 337.

Wells, "Additivity of Mutational Effects in Proteins," Biochemistry, Sep. 1990, vol. 29(37), pp. 8509-8517.

Wells, "Hematopoietic Receptor Complexes," Ann. Rev. Biochem., 1996, vol. 65, pp. 609-634.

Yamasaki et al., "Effect of Divalent Polyethylene Glycol Units, Conjugated on Human Granulocyte Colony-Stimulating Factor, on Biological Activities In vitro and In Vivo," Drugs Exptl.Clin. Res., 1998, vol. 24(4), pp. 191-196.

Youngster et al. "Structure, biology, and therapeutic implications of pegylated interferon alpha-2b," Current Pharmaceutical Design, Nov. 2002, vol. 8, No. 24, pp. 2139-2157.

Zalipsky, "Chemistry of polyethylene glycol conjugates with biologically active molecules," Adv. Drug Delivery Reviews, 1995, vol. 16, pp. 157-182.

Zhang et al., "Characterization of asparagine deamidation and aspartate isomerization in recombinant human interleukin-11," Pharmaceutical Research, Aug. 2002, vol. 19(8), pp. 1223-1231.

Zurawaki et al., "Definition and spatial location of mouse interleukin-2 residues that interact with the heterotrmeric receptor," Embo Journal, 1993, vol. 12, pp. 5113-5119.

International Preliminary Examination Report for International (PCT) Patent Application No. PCT/US98/14497, mailed May 11, 1999.

International Search Report for International (PCT) Patent Application No. PCT/US98/14497, mailed Oct. 22, 1998.

Chen et al., "Construction, properties and specific fluorescent labeling of a bovine prothrombin mutant engineered with a free C-terminal cysteine," Protein Engr., 1996, vol. 9(6), pp. 545-533.

"Dulbecco's Modified Eagle's Medium/Ham's Nutrient Mixture F12," product information, SAFC Biosciences, Inc., 2006, 2 pages.

McElroy et al., "Structural and Biophysical Studies of the Human IL-7/IL-7Rα Complex," Structure, 2009, vol. 17(1), pp. 54-65, NIH Public Acess Author Manuscript, 25 pages.

Petoukov et al., "Addition of Missing Loops and Domains to Protein Models by X-Ray Solution Scattering," Biophys. J., 2002, vol. 83, pp. 3113-3125.

Takahashi et al., "Beneficial Effect of Brewers' Yeast Extract on Daily Activity in a Murine Model of Chronic Fatigue Syndrome," Advance Access Publication, eCAM, Jan. 23, 2006, vol. 3(1), pp. 109-115.

METHODS OF TREATMENT USING CYSTEINE VARIANTS OF INTERLEUKIN-11

CROSS-REFERENCE TO RELATED APPLICATIONS

This application is a Continuation of U.S. application Ser. No. 12/391,896, filed Feb. 24, 2009, now U.S. Pat. No. 8,133,480, which is a Continuation of U.S. application Ser. No. 11/544,473, filed Oct. 5, 2006, now U.S. Pat. No. 7,495,087, which claims the benefit of priority under 35 U.S.C. §119(e) from U.S. Provisional Application No. 60/724,204, filed Oct. 5, 2005. U.S. application Ser. No. 11/544,473 is also a continuation-in-part of U.S. application Ser. No. 10/298,148, filed Nov. 15, 2002, now U.S. Pat. No. 7,153,943, which claims the benefit of priority under 35 U.S.C. §119(e) from U.S. Provisional Application Ser. No. 60/332,285, filed Nov. 15, 2001, and from U.S. Provisional Application Ser. No. 60/418,040, filed Oct. 11, 2002. U.S. application Ser. No. 10/298,148 is a continuation-in-part of U.S. application Ser. No. 09/462,941, filed Jan. 14, 2000, now U.S. Pat. No. 6,608,183, which is a national stage filing under 35 U.S.C. 371 of PCT Application Serial No. PCT/US98/14497, filed Jul. 13, 1998, and which claims the benefit of priority from U.S. Provisional Application Ser. No. 60/052,516, filed Jul. 14, 1997. The entire disclosure of each of the above-identified applications is incorporated herein by reference.

GOVERNMENT SUPPORT

This invention was made in part with government support under NIH Grant No. 1R43 CA084851 and NIH Grant No. 2R44CA084851, each awarded by the National Institutes of Health. The government has certain rights to this invention.

REFERENCE TO SEQUENCE LISTING

This application contains a Sequence Listing submitted on a compact disc, in duplicate. Each of the two compact discs, which are identical to each other pursuant to 37 CFR §1.52 (e)(4), contains the following file: "4152-1-PUS-14.ST25.txt", having a size in bytes of 45 KB, recorded on 5 Oct. 2006. The information contained on the compact disc is hereby incorporated by reference in its entirety pursuant to 37 CFR §1.77(b)(4).

FIELD OF THE INVENTION

The present invention relates to genetically engineered therapeutic proteins and methods of use thereof. More specifically, the engineered proteins include cysteine variants of the growth hormone supergene family, such as interleukin-11 (IL-11) and related proteins, and methods of making and using such proteins.

BACKGROUND OF THE INVENTION

The following proteins are encoded by genes of the growth hormone (GH) supergene family (Bazan (1990); Mott and Campbell (1995); Silvennoinen and Ihle (1996)): growth hormone, prolactin, placental lactogen, erythropoietin (EPO), thrombopoietin (TPO), interleukin-2 (IL-2), IL-3, IL-4, IL-5, IL-6, IL-7, IL-9, IL-10, IL-11, IL-12 (p35 subunit), IL-13, IL-15, oncostatin M, ciliary neurotrophic factor, leukemia inhibitory factor, alpha interferon, beta interferon, gamma interferon, omega interferon, tau interferon, granulocyte-colony stimulating factor (G-CSF), granulocyte-macrophage colony stimulating factor (GM-CSF), macrophage colony stimulating factor (M-CSF) and cardiotrophin-1 (CT-1) ("the GH supergene family"). It is anticipated that additional members of this gene family will be identified in the future through gene cloning and sequencing. Members of the GH supergene family have similar secondary and tertiary structures, despite the fact that they generally have limited amino acid or DNA sequence identity. The shared structural features allow new members of the gene family to be readily identified.

There is considerable interest on the part of patients and healthcare providers in the development of long acting, "user-friendly" protein therapeutics. Proteins are expensive to manufacture and, unlike conventional small molecule drugs, are not readily absorbed by the body. Moreover, they are digested if taken orally. Therefore, natural proteins must be administered by injection. After injection, most proteins are cleared rapidly from the body, necessitating frequent, often daily, injections. Patients dislike injections, which leads to reduced compliance and reduced drug efficacy. Some proteins, such as erythropoietin (EPO), are effective when administered less often (three times per week for EPO) because they are glycosylated. However, glycosylated proteins are produced using expensive mammalian cell expression systems.

The length of time an injected protein remains in the body is finite and is determined by, e.g., the protein's size and whether or not the protein contains covalent modifications such as glycosylation. Circulating concentrations of injected proteins change constantly, often by several orders of magnitude, over a 24-hour period. Rapidly changing concentrations of protein agonists can have dramatic downstream consequences, at times under-stimulating and at other times over-stimulating target cells. Similar problems plague protein antagonists. These fluctuations can lead to decreased efficacy and increased frequency of adverse side effects for protein therapeutics. The rapid clearance of recombinant proteins from the body significantly increases the amount of protein required per patient and dramatically increases the cost of treatment. The cost of human protein pharmaceuticals is expected to increase dramatically in the years ahead as new and existing drugs are approved for more disease indications. Thus, there is a need to develop protein technologies that improve the efficacy of protein therapeutics, lessen the need for frequent delivery, and lower the costs of protein therapeutics to patients and healthcare providers.

SUMMARY OF THE INVENTION

One embodiment of the present invention relates to a method to treat an animal with a disease or condition that can be treated by wild-type interleukin-11 (IL-11), to stimulate platelet production in an animal, or to accelerate an animal's recovery from thrombocytopenia. The method includes administering to the animal an interleukin-11 (IL-11) cysteine mutein, wherein the mutein has biological activity in vitro as measured by proliferation of a cell line that proliferates in response to IL-11. The thrombocytopenia can include, but is not limited to: (a) thrombocytopenia resulting from myelosuppressive chemotherapy; (b) thrombocytopenia resulting from other chemical treatments; (c) thrombocytopenia resulting from radiological treatments; (d) thrombocytopenia resulting from disease; (e) thrombocytopenia resulting from idiopathic causes; (f) thrombocytopenia resulting from drug treatments, including interferons and ribavarin; (g) thrombocytopenia in neonates; (h) thrombocytopenia resulting from myelodysplastic syndromes; (i) thrombocytopenia resulting from aplastic anemia; and (j) thrombocytopenia resulting from cirrhosis. In one aspect, the thrombocytopenia is thrombocytopenia resulting from myelosuppressive chemotherapy.

In one aspect of this embodiment, the IL-11 cysteine mutein comprises at least one non-native cysteine residue which has been added, either by substitution for an amino acid in the natural protein sequence or by insertion between two adjacent amino acids in the natural protein sequence, in a region of the protein selected from: the A-B loop, the B-C loop, the C-D loop, the first three or last three amino acids in helix A, the first three or last three amino acids in helix B, the first three or last three amino acids in helix C, the first three or last three amino acids in helix D, the amino acids preceding helix A, and the amino acids following helix D, wherein the mutein has biological activity in vitro as measured by proliferation of a cell line that proliferates in response to IL-11. In one aspect of this embodiment, the IL-11 cysteine mutein comprises at least one non-native cysteine residue which has been added preceding the N-terminal amino acid of the mature protein or following the C-terminal amino acid of the protein, wherein the mutein has biological activity in vitro as measured by proliferation of a cell line that proliferates in response to IL-11. In one aspect, the cysteine mutein comprises at least one cysteine residue substituted for an amino acid in wild-type IL-11 (SEQ ID NO:17) at a position selected from: any of positions 22-36, any of positions 37-39, any of positions 54-56, any of positions 57-91, any of positions 92-94, any of positions 110-112, any of positions 113-124, any of positions 125-127, any of positions 145-147, any of positions 148-172, any of positions 173-175, any of positions 194-196, and any of positions 197-199, wherein the mutein has biological activity in vitro as measured by proliferation of a cell line that proliferates in response to IL-11. In another aspect, the cysteine mutein comprises at least one cysteine residue substituted for an amino acid selected in SEQ ID NO:17 from: P22, G23, P24, P25, P26, G27, E38, L39, D69, L72, S74, T77, A114, S117, E123, A148, Q151, A158, A162, and S165, wherein the mutein has biological activity in vitro as measured by proliferation of a cell line that proliferates in response to IL-11. In another aspect, the cysteine mutein comprises at least two cysteine substitutions, wherein a cysteine residue is substituted for an amino acid in SEQ ID NO:17 selected from: P25 and T77, P25 and S117, P25 and S165, P24 and P25, D69 and T77, and A162 and S165, wherein the mutein has biological activity in vitro as measured by proliferation of a cell line that proliferates in response to IL-11.

In one aspect of this embodiment, the cysteine mutein is modified with at least one polyethylene glycol. In another aspect, the IL-11 cysteine mutein is modified with a cysteine-reactive moiety, including, but not limited to, polyethylene glycol.

The cysteine mutein can be administered by a route including, but not limited to, intravenous administration, intraperitoneal administration, intramuscular administration, intranodal administration, intracoronary administration, intraarterial administration, subcutaneous administration, transdermal delivery, intratracheal administration, intraarticular administration, intraventricular administration, inhalation, intranasal, intracranial, intraspinal, intraocular, aural, oral, pulmonary administration, impregnation of a catheter, and direct injection into a tissue.

Another embodiment of the invention relates to a cysteine mutein of interleukin-11 (IL-11) of SEQ ID NO:17, wherein a cysteine residue is substituted for at least one amino acid selected from: P22, G23, P24, P25, P26, G27, E38, L39, D69, L72, S74, T77, A114, S117, E123, A148, Q151, A158, A162, and S165, wherein the mutein has biological activity in vitro as measured by proliferation of a cell line that proliferates in response to IL-11. In one aspect of this embodiment, the cysteine mutein comprises at least two cysteine substitutions, wherein a cysteine residue is substituted for an amino acid in SEQ ID NO:17 selected from: P25 and T77, P25 and S117, P25 and S165, P24 and P25, D69 and T77, and A162 and S165, and wherein the mutein has biological activity in vitro as measured by proliferation of a cell line that proliferates in response to IL-11. In another aspect, the substituted cysteine residue is modified with at least one polyethylene glycol. In one aspect, the cysteine mutein is modified with a cysteine-reactive moiety, including, but not limited to, polyethylene glycol.

Another embodiment of the present invention relates to a composition including any of the IL-11 cysteine variants described herein, and a pharmaceutically acceptable carrier.

Another embodiment of the present invention relates to a method to stimulate platelet production in an animal, or to accelerate an animal's recovery from thrombocytopenia, which includes administering to the animal any of the IL-11 cysteine muteins described above.

Yet another embodiment of the present invention relates to a method to produce a cysteine mutein of IL-11. Such a method includes the steps of production and purification of the IL-11 mutein using an insect system as described in any of Examples 2-4, using an *E. coli* system as described in Examples 7-8, or using an *E. coli* intein system as described in Example 9.

DETAILED DESCRIPTION OF THE INVENTION

The present invention provides a solution to problems associated with protein therapeutics by providing methods to prolong the circulating half-lives of protein therapeutics in the body so that the proteins do not have to be injected frequently. This solution also satisfies the needs and desires of patients for protein therapeutics that are "user-friendly", i.e., protein therapeutics that do not require frequent injections. The present invention solves these and other problems by providing biologically active, cysteine-added variants of members of the growth hormone supergene family, and in particular, interleukin-11 (IL-11). The invention also provides for the chemical modification of these variants with cysteine-reactive polymers or other types of cysteine-reactive moieties to produce derivatives thereof and the molecules so produced. The invention also provides for therapeutic methods using the protein variants described herein.

Accordingly, the present invention relates to cysteine variants and particularly, cysteine variants of IL-11, and, among other things, the site-specific conjugation of such proteins with polyethylene glycol (PEG) or other such moieties. PEG is a non-antigenic, inert polymer that significantly prolongs the length of time a protein circulates in the body. This allows the protein to be effective for a longer period of time. Covalent modification of proteins with PEG has proven to be a useful method to extend the circulating half-lives of proteins in the body (Abuchowski et al., 1984; Hershfield, 1987; Meyers et al., 1991). Covalent attachment of PEG to a protein increases the protein's effective size and reduces its rate of clearance rate from the body. PEGs are commercially available in several sizes, allowing the circulating half-lives of PEG-modified proteins to be tailored for individual indications through use of different size PEGs. Other benefits of PEG modification include an increase in protein solubility, an increase in in vivo protein stability and a decrease in protein immunogenicity (Katre et al., 1987; Katre, 1990).

A preferred method for PEGylating proteins is to covalently attach PEG to cysteine residues using cysteine-reactive PEGs. A number of highly specific, cysteine-reactive PEGs with different reactive groups (e.g., maleimide, vinylsulfone) and different size PEGs (2-20 kDa) are commercially available (e.g., from Shearwater, Polymers, Inc., Huntsville, Ala.). At neutral pH, these PEG reagents selectively attach to "free" cysteine residues, i.e., cysteine residues not involved in disulfide bonds. The conjugates are hydrolytically stable. Use of cysteine-reactive PEGs allows the development of homogeneous PEG-protein conjugates of defined structure.

Considerable progress has been made in recent years in determining the structures of commercially important protein therapeutics and understanding how they interact with their protein targets, e.g., cell-surface receptors, proteases, etc. This structural information can be used to design PEG-protein conjugates using cysteine-reactive PEGs. Cysteine residues in most proteins participate in disulfide bonds and are not available for PEGylation using cysteine-reactive PEGs. Through in vitro mutagenesis using recombinant DNA techniques, additional cysteine residues can be introduced anywhere into the protein. The added cysteines can be introduced at the beginning of the protein, at the end of the protein, between two amino acids in the protein sequence or, preferably, substituted for an existing amino acid in the protein sequence. The newly added "free" cysteines can serve as sites for the specific attachment of a PEG molecule using cysteine-reactive PEGs. The added cysteine must be exposed on the protein's surface and accessible for PEGylation for this method to be successful. If the site used to introduce an added cysteine site is non-essential for biological activity, then the PEGylated protein will display essentially wild type (normal) in vitro bioactivity. The major technical challenge in PEGylating proteins with cysteine-reactive PEGs is the identification of surface exposed, non-essential regions in the target protein where cysteine residues can be added or substituted for existing amino acids without loss of bioactivity.

Cysteine-added variants of a few human proteins and PEG-polymer conjugates of these proteins have been described. U.S. Pat. No. 5,206,344 describes cysteine-added variants of IL-2. These cysteine-added variants are located within the first 20 amino acids from the amino terminus of the mature IL-2 polypeptide chain. The preferred cysteine variant is at position 3 of the mature polypeptide chain, which corresponds to a threonine residue that is O-glycosylated in the naturally occurring protein. Substitution of cysteine for threonine at position 3 yields an IL-2 variant that can be PEGylated with a cysteine-reactive PEG and retain full in vitro bioactivity (Goodson and Katre, 1990). In contrast, natural IL-2 PEGylated with lysine-reactive PEGs displays reduced in vitro bioactivity (Goodson and Katre, 1990). The effects of cysteine substitutions at other positions in IL-2 were not reported.

U.S. Pat. No. 5,166,322 teaches cysteine-added variants of IL-3. These variants are located within the first 14 amino acids from the N-terminus of the mature protein sequence. The patent teaches expression of the proteins in bacteria and covalent modification of the proteins with cysteine-reactive PEGs. No information is provided as to whether the cysteine-added variants and PEG-conjugates of IL-3 are biologically active. Cysteine-added variants at other positions in the polypeptide chain were not reported.

PCT Patent Publication No. WO 9412219 and PCT Patent Application No. PCT/US95/06540 teach cysteine-added variants of insulin-like growth factor-I (IGF-I). IGF-I has a very different structure from GH and is not a member of the GH supergene family (Mott and Campbell, 1995). Cysteine substitutions at many positions in the IGF-I protein are described. Only certain of the cysteine-added variants are biologically active. The preferred site for the cysteine added variant is at amino acid position 69 in the mature protein chain. Cysteine substitutions at positions near the N-terminus of the protein (residues 1-3) yielded IGF-I variants with reduced biological activities and improper disulfide bonds.

PCT Patent Publication No. WO 94/22466 teaches two cysteine-added variants of insulin-like growth factor (IGF) binding protein-1, which has a very different structure than GH and is not a member of the GH supergene family. The two cysteine-added IGF binding protein-1 variants disclosed are located at positions 98 and 101 in the mature protein chain and correspond to serine residues that are phosphorylated in the naturally-occurring protein.

U.S. patent application Ser. No. 07/822,296 teaches cysteine added variants of tumor necrosis factor binding protein, which is a soluble, truncated form of the tumor necrosis factor cellular receptor. Tumor necrosis factor binding protein has a very different structure than GH and is not a member of the GH supergene family.

IGF-I, IGF binding protein-1 and tumor necrosis factor binding protein have secondary and tertiary structures that are very different from GH and the proteins are not members of the GH supergene family. Because of this, it is difficult to use the information gained from studies of IGF-I, IGF binding protein-1 and tumor necrosis factor binding protein to create cysteine-added variants of members of the GH supergene family. The studies with IL-2 and IL-3 were carried out before the structures of IL-2 and IL-3 were known (McKay 1992; Bazan, 1992) and before it was known that these proteins are members of the GH supergene family. Previous experiments aimed at identifying preferred sites for adding cysteine residues to IL-2 and IL-3 were largely empirical and were performed prior to experiments indicating that members of the GH supergene family possessed similar secondary and tertiary structures.

Based on the structural information now available for members of the GH supergene family, the present invention provides "rules" for determining a priori which regions and amino acid residues in members of the GH supergene family can be used to introduce or substitute cysteine residues without significant loss of biological activity. In contrast to the naturally occurring proteins, these cysteine-added variants of members of the GH supergene family will possess novel properties such as the ability to be covalently modified at defined sites within the polypeptide chain with cysteine-reactive polymers or other types of cysteine-reactive moieties. The covalently modified proteins will be biologically active.

GH is the best-studied member of the GH supergene family. GH is a 22 kDa protein secreted by the pituitary gland. GH stimulates metabolism of bone, cartilage and muscle and is the body's primary hormone for stimulating somatic growth during childhood. Recombinant human GH (rhGH) is used to treat short stature resulting from GH inadequacy and renal failure in children. GH is not glycosylated and can be produced in a fully active form in bacteria. The protein has a short in vivo half-life and must be administered by daily subcutaneous injection for maximum effectiveness (MacGillivray et al., 1996). Recombinant human GH (rhGH) was approved recently for treating cachexia in AIDS patients and is under study for treating cachexia associated with other diseases.

The sequence of human GH is well known (see, e.g., Martial et al. 1979; Goeddel et al. 1979 which are incorporated herein by reference; SEQ ID NO:1). GH is closely related in sequence to prolactin and placental lactogen and these three proteins were considered originally to comprise a small gene family. The primary sequence of GH is highly conserved among animal species (Abdel-Meguid et al., 1987), consistent with the protein's broad species cross-reactivity. The three dimensional folding pattern of porcine GH has been solved by X-ray crystallography (Abdel-Meguid et al., 1987). The protein has a compact globular structure, comprising four amphipathic alpha helical bundles joined by loops. Human GH has a similar structure (de Vos et al., 1992). The four alpha helical regions are termed A-D beginning from the N-terminus of the protein. The loop regions are referred to by the helical regions they join, e.g., the A-B loop joins helical bundles A and B. The A-B and C-D loops are long, whereas the B-C loop is short. GH contains four cysteine residues, all of which participate in disulfide bonds. The disulfide assignments are cysteine-53 joined to cysteine-165 and cysteine-182 joined to cysteine-189.

The crystal structure of GH bound to its receptor revealed that GH has two receptor binding sites and binds two receptor molecules (Cunningham et al., 1991; de Vos et al., 1992). The two receptor binding sites are referred to as site I and site II. Site I encompasses the Carboxy (C)-terminal end of helix D and parts of helix A and the A-B loop, whereas site II encompasses the Amino (N)-terminal region of helix A and a portion of helix C. Binding of GH to its receptor occurs sequentially, with site I always binding first. Site II then engages a second GH receptor, resulting in receptor dimerization and activation of the intracellular signaling pathways that lead to cellular responses to GH. A GH mutein in which site II has been mutated (a glycine to arginine mutation at amino acid 120) is able to bind a single GH receptor, but is unable to dimerize GH receptors; this mutein acts as a GH antagonist in vitro, presumably by occupying GH receptor sites without activating intracellular signaling pathways (Fuh et al., 1992).

The roles of particular regions and amino acids in GH receptor binding and intracellular signaling also have been studied using techniques such as mutagenesis, monoclonal antibodies and proteolytic digestion. The first mutagenesis experiments entailed replacing entire domains of GH with similar regions of the closely related protein, prolactin (Cunningham et al., 1989). One finding was that replacement of the B-C loop of GH with that of prolactin did not affect binding of the hybrid GH protein to a soluble form of the human GH receptor, implying that the B-C loop was non-essential for receptor binding. Alanine scanning mutagenesis (replacement of individual amino acids with alanine) identified 14 amino acids that are critical for GH bioactivity (Cunningham and Wells, 1989). These amino acids are located in the helices A, B, C, and D and the A-B loop and correspond to sites I and II identified from the structural studies. Two lysine residues at amino acid positions 41 and 172, K41 and K172, were determined to be critical components of the site I receptor binding site, which explains the decrease in bioactivity observed when K172 is acetylated (Teh and Chapman, 1988). Modification of K168 also significantly reduced GH receptor binding and bioactivity (de la Llosa et al., 1985; Martal et al., 1985; Teh and Chapman, 1988). Regions of GH responsible for binding the GH receptor have also been studied using monoclonal antibodies (Cunningham et al., 1989). A series of eight monoclonal antibodies was generated to human GH and analyzed for the ability to neutralize GH activity and prevent binding of GH to its recombinant soluble receptor. The latter studies allowed the putative binding site for each monoclonal antibody to be localized within the GH three-dimensional structure. Of interest was that monoclonal antibodies 1 and 8 were unable to displace GH from binding its receptor. The binding sites for these monoclonal antibodies were localized to the B-C loop (monoclonal number 1) and the N-terminal end of the A-B loop (monoclonal number 8). No monoclonals were studied that bound the C-D loop specifically. The monoclonal antibody studies suggest that the B-C loop and N-terminal end of the A-B loop are non-essential for receptor binding. Finally, limited cleavage of GH with trypsin was found to produce a two chain derivative that retained full activity (Mills et al., 1980; Li, 1982). Mapping studies indicated that trypsin cleaved and/or deleted amino acids between positions 134 and 149, which corresponds to the C-D loop. These studies suggest the C-D loop is not involved in receptor binding or GH bioactivity.

Structures of a number of cytokines, including G-CSF (Hill et al., 1993), GM-CSF (Diederichs et al., 1991; Walter et al., 1992), IL-2 (Bazan, 1992; McKay, 1992), IL-4 (Redfield et al., 1991; Powers et al., 1992), and IL-5 (Milburn et al., 1993) have been determined by X-ray diffraction and NMR studies and show striking conservation with the GH structure, despite a lack of significant primary sequence homology. EPO is considered to be a member of this family based upon modeling and mutagenesis studies (Boissel et al., 1993; Wen et al., 1994). A large number of additional cytokines and growth factors including ciliary neurotrophic factor (CNTF), leukemia inhibitory factor (LIF), thrombopoietin (TPO), oncostatin M, macrophage colony stimulating factor (M-CSF), IL-3, IL-6, IL-7, IL-9, IL-12, IL-13, IL-15, and alpha, beta, omega, tau and gamma interferon belong to this family (reviewed in Mott and Campbell, 1995; Silvennoinen and Ihle 1996). All of the above cytokines and growth factors are now considered to comprise one large gene family, of which GH is the prototype.

In addition to sharing similar secondary and tertiary structures, members of this family share the property that they must oligomerize cell surface receptors to activate intracellular signaling pathways. Some GH family members, e.g., GH and EPO, bind a single type of receptor and cause it to form homodimers. Other family members, e.g., IL-2, IL-4, and IL-6, bind more than one type of receptor and cause the receptors to form heterodimers or higher order aggregates (Davis et al., 1993; Paonessa et al., 1995; Mott and Campbell, 1995). Mutagenesis studies have shown that, like GH, these other cytokines and growth factors contain multiple receptor binding sites, typically two, and bind their cognate receptors sequentially (Mott and Campbell, 1995; Matthews et al., 1996). Like GH, the primary receptor binding sites for these other family members occur primarily in the four alpha helices and the A-B loop (reviewed in Mott and Campbell, 1995). The specific amino acids in the helical bundles that participate in receptor binding differ amongst the family members (Mott and Campbell, 1995). Most of the cell surface receptors that interact with members of the GH supergene family are structurally related and comprise a second large multi-gene family (Bazan, 1990; Mott and Campbell, 1995; Silvennoinen and Ihle 1996).

A general conclusion reached from mutational studies of various members of the GH supergene family is that the loops joining the alpha helices generally tend to not be involved in receptor binding. In particular the short B-C loop appears to be non-essential for receptor binding in most, if not all, family members. For this reason, the B-C loop is a preferred region for introducing cysteine substitutions in members of the GH supergene family. The A-B loop, the B-C loop, the C-D loop (and D-E loop of interferon/IL-10-like members of the GH superfamily) also are preferred sites for introducing cysteine mutations. Amino acids proximal to helix A and distal to the final helix also tend not to be involved in receptor binding and also are preferred sites for introducing cysteine substitutions.

Certain members of the GH family, e.g., EPO, IL-2, IL-3, IL-4, IL-6, G-CSF, GM-CSF, TPO, IL-10, IL-12 p35, IL-13, IL-15 and beta-interferon contain N-linked and O-linked sugars. The glycosylation sites in the proteins occur almost exclusively in the loop regions and not in the alpha helical bundles. Because the loop regions generally are not involved in receptor binding and because they are sites for the covalent attachment of sugar groups, they are preferred sites for introducing cysteine substitutions into the proteins Amino acids that comprise the N- and O-linked glycosylation sites in the proteins are preferred sites for cysteine substitutions because these amino acids are surface-exposed, the natural protein can tolerate bulky sugar groups attached to the proteins at these sites and the glycosylation sites tend to be located away from the receptor binding sites.

Many additional members of the GH gene family are likely to be discovered in the future. New members of the GH supergene family can be identified through computer-aided secondary and tertiary structure analyses of the predicted protein sequences. Members of the GH supergene family will possess four or five amphipathic helices joined by non-helical amino acids (the loop regions). The proteins may contain a hydrophobic signal sequence at their N-terminus to promote secretion from the cell. Such later discovered members of the GH supergene family also are included within this invention.

The present invention provides "rules" for creating biologically active cysteine-added variants of members of the GH supergene family. These "rules" can be applied to any existing or future member of the GH supergene family. The cysteine-added variants will posses novel properties not shared by the naturally occurring proteins. Most importantly, the cysteine added variants will possess the property that they can be covalently modified with cysteine-reactive polymers or other types of cysteine-reactive moieties to generate biologically active proteins with improved properties such as increased in vivo half-life, increased solubility and improved in vivo efficacy.

Specifically, the present invention provides biologically active cysteine variants of members of the GH supergene family by substituting cysteine residues for non-essential amino acids in the proteins. Preferably, the cysteine residues are substituted for amino acids that comprise the loop regions, for amino acids near the ends of the alpha helices and for amino acids proximal to (preceding) the first amphipathic helix or distal to (following) the final amphipathic helix of these proteins. Other preferred sites for adding cysteine residues are at the N-terminus or C-terminus of the proteins. Cysteine residues also can be introduced between two amino acids in the disclosed regions of the polypeptide chain. The present invention teaches that N- and O-linked glycosylation sites in the proteins are preferred sites for introducing cysteine substitutions either by substitution for amino acids that make up the sites or, in the case of N-linked sites, introduction of cysteines therein. The glycosylation sites can be serine or threonine residues that are O-glycosylated or asparagine residues that are N-glycosylated. N-linked glycosylation sites have the general structure asparagine-X-serine or threonine (N-X-S/T), where X can be any amino acid. The asparagine residue, the amino acid in the X position and the serine/threonine residue of the N-linked glycosylation site are preferred sites for creating biologically active cysteine-added variants of these proteins. Amino acids immediately surrounding or adjacent to the O-linked and N-linked glycosylation sites (within about 10 residues on either side of the glycosylation site) are preferred sites for introducing cysteine-substitutions.

More generally, certain of the "rules" for identifying preferred sites for creating biologically active cysteine-added protein variants can be applied to any protein, not just proteins that are members of the GH supergene family. Specifically, preferred sites for creating biologically active cysteine variants of proteins (other than IL-2) are O-linked glycosylation sites. Amino acids immediately surrounding the O-linked glycosylation site (within about 10 residues on either side of the glycosylation site) also are preferred sites. N-linked glycosylation sites, and the amino acid residues immediately adjacent on either side of the glycosylation site (within about 10 residues of the N-X-S/T site) also are preferred sites for creating cysteine added protein variants. Amino acids that can be replaced with cysteine without significant loss of biological activity also are preferred sites for creating cysteine-added protein variants. Such non-essential amino acids can be identified by performing cysteine-scanning mutagenesis on the target protein and measuring effects on biological activity. Cysteine-scanning mutagenesis entails adding or substituting cysteine residues for individual amino acids in the polypeptide chain and determining the effect of the cysteine substitution on biological activity. Cysteine scanning mutagenesis is similar to alanine-scanning mutagenesis (Cunningham et al., 1992), except that target amino acids are individually replaced with cysteine rather than alanine residues.

Application of the "rules" to create cysteine-added variants and conjugates of protein antagonists also is contemplated. Excess production of cytokines and growth factors has been implicated in the pathology of many inflammatory conditions such as rheumatoid arthritis, asthma, allergies and wound scarring. Excess production of GH has been implicated as a cause of acromegaly. Certain growth factors and cytokines, e.g., GH and IL-6, have been implicated in proliferation of particular cancers. Many of the growth factors and cytokines implicated in inflammation and cancer are members of the GH supergene family. There is considerable interest in developing protein antagonists of these molecules to treat these diseases. One strategy involves engineering the cytokines and growth factors so that they can bind to, but not oligomerize receptors. This is accomplished by mutagenizing the second receptor binding site (site II) on the molecules. The resulting muteins are able to bind and occupy receptor sites but are incapable of activating intracellular signaling pathways. This strategy has been successfully applied to GH to make a GH antagonist (Cunningham et al., 1992). Similar strategies are being pursued to develop antagonists of other members of the GH supergene family such as IL-2 (Zurawski et al., 1990; Zurawski and Zurawski, 1992), IL-4 (Kruse et al., 1992), IL-5 (Tavernier et al., 1995), GM-CSF (Hercus et al., 1994) and EPO (Matthews et al., 1996). Since the preferred sites for adding cysteine residues to members of the GH supergene family described here lie outside of the receptor binding sites in these proteins, and thus removed from any sites used to create protein antagonists, the cysteine-added variants described herein could be used to generate long-acting versions of protein antagonists. As an example, Cunningham et al. (1992) developed an in vitro GH antagonist by mutating a glycine residue (amino acid 120) to an arginine. This glycine residue is a critical component of the second receptor binding site in GH; when it is replaced with arginine, GH cannot dimerize receptors. The glycine to arginine mutation at position 120 can be introduced into DNA sequences encoding the cysteine-added variants of GH contemplated herein to create a cysteine-added GH antagonist that can be conjugated with cysteine-reactive PEGs or other types of cysteine-reactive moieties. Similarly, amino acid changes in other proteins that turn the proteins from agonists to antagonists could be incorporated into DNA sequences encoding cysteine-added protein variants described herein. Considerable effort is being spent to identify amino acid changes that convert protein agonists to antagonists. Hercus et al. (1994) reported that substituting arginine or lysine for glutamic acid at position 21 in the mature GM-CSF protein converts GM-CSF from an agonist to an antagonist. Tavernier et al. (1995) reported that substituting glutamine for glutamic acid at position 13 of mature IL-5 creates an IL-5 antagonist.

Experimental strategies similar to those described above can be used to create cysteine-added variants (both agonists and antagonists) of members of the GH supergene family derived from various animals. This is possible because the primary amino acid sequences and structures of cytokines and growth factors are largely conserved between human and animal species. For this reason, the "rules" disclosed herein for creating biologically active cysteine-added variants of members of the GH supergene family will be useful for creating biologically active cysteine-added variants of members of the GH supergene family of companion animals (e.g., dogs, cats, horses) and commercial animal (e.g., cow, sheep, pig) species. Conjugation of these cysteine-added variants with cysteine-reactive PEGs will create long-acting versions of these proteins that will benefit the companion animal and commercial farm animal markets. Proteins that are members of the GH supergene family (hematopoietic cytokines) are provided in Silvennoimem and Ihle (1996). Silvennoimem and Ihle (1996) also provide information about the structure and expression of these proteins. DNA sequences, encoded amino acids and in vitro and in vivo bioassays for the proteins described herein are described in Aggarwal and Gutterman (1992; 1996), Aggarwal (1998), and Silvennoimem and Ihle (1996). Bioassays for the proteins also are provided in catalogues of various commercial suppliers of these proteins such as R&D Systems, Inc. and Endogen, Inc.

The cysteine variants of the present invention can be used for any of the known therapeutic uses of the native proteins in essentially the same forms and doses all well known in the art. By way of example, therapeutic methods for stimulating platelet production in a patient and for accelerating recovery from and/or reducing the severity of thrombocytopenia in a patient are described herein, which use cysteine variants of interleukin-11 (IL-11) according to the present invention. It is to be understood, however, that general discussion regarding modes of administration, dosage and delivery of cysteine variants such as the IL-11 muteins, is generally intended to apply to therapeutic methods using any of the cysteine variants or other PEGylated or cysteine-modified IL-11 proteins described herein.

One embodiment of the present invention relates to cysteine muteins of IL-11, and methods of making and using such muteins (also referred to herein as IL-11 cysteine variants). IL-11 is a pleiotropic cytokine that stimulates hematopoiesis, lymphopoeisis and acute phase responses. The amino acid sequence of human IL-11 (represented herein by SEQ ID NO:17) is given in Kawashima et al. (1991) and Paul et al. (1990) both incorporated herein by reference. IL-11 is synthesized as a precursor protein of 199 amino acids that is cleaved to yield a mature protein of 178 amino acids. There are no N-linked glycosylation sites in the protein. IL-11 has four major alpha helices referred to as helices A-D. Relative to the amino acid sequence shown in SEQ ID NO:17, helix A encompasses amino acids 37-56, helix B encompasses amino acids 92-112, helix C encompasses amino acids 125-147 and helix D encompasses amino acids 173-196. Amino acids 1-21 of SEQ ID NO:17 encompass the IL-11 signal sequence.

This invention provides cysteine-added variants of IL-11, wherein cysteine substitutions or insertions are made in one or more of the region proximal to (preceding) the A helix (amino acids 22-36 of SEQ ID NO:17), distal to (following) the D helix (amino acids 197-199 of SEQ ID NO:17), in the A-B loop (amino acids 57-91 of SEQ ID NO:17), in the B-C loop (amino acids 113-124 of SEQ ID NO:17), and in the C-D loop (amino acids 148-172 of SEQ ID NO:17). This invention also provides cysteine-added variants at the first three or last three amino acids in any one or more of helices A, B, C and D. Variants in which cysteine residues are added proximal to the first amino acid of the mature protein (amino acid 22 of SEQ ID NO:17) or distal to the final amino acid of the mature protein (amino acid 199 of SEQ ID NO:17) also are provided. Any individual amino acid encompassed by the above-identified disclosure of regions is expressly included as a residue for cysteine substitution, or before or after which a cysteine can be inserted, according to the present invention.

Preferred site for cysteine substitutions in the region preceding helix A of IL-11 are (relative to SEQ ID NO:17): P22, G23, P24, P25, P26, G27, P28, P29, R30, V31, S32, P33, D34, P35, and R36. Preferred sites for cysteine substitutions in the A-B loop of IL-11 are (relative to SEQ ID NO:17): A57, A58, Q59, L60, R61, D62, K63, F64, P65, A66, D67, G68, D69, H70, N71, L72, D73, S74, L75, P76, T77, L78, A79, M80, S81, A82, G83, A84, L85, G86, A87, L88, Q89, L90, and P91. Preferred sites for cysteine substitutions in the C-D loop of IL-11 are (relative to SEQ ID NO:17): A148, L149, P150, Q151, P152, P153, P154, D155, P156, P157, A158, P159, P160, L161, A162, P163, P164, S165, 5166, A167, W168, G169, G170, I171, and R172. Preferred sites for cysteine substitutions in region following helix D of IL-11 are (relative to SEQ ID NO:17): T197, R198, and L199. Preferred sites for cysteine substitutions in the first 3 amino acids of helix A are (relative to SEQ ID NO:17): A37, D38, and L39. Preferred sites for cysteine substitutions in the last 3 amino acids of helix A are (relative to SEQ ID NO:17): R54, Q55, and L56. Preferred sites for cysteine substitutions in the first 3 amino acids of helix B are (relative to SEQ ID NO:17): G92, V93, and L94. Preferred sites for cysteine substitutions in the last 3 amino acids of helix B are (relative to SEQ ID NO:17): W110, L111, and R112. Preferred sites for cysteine substitutions in the first 3 amino acids of helix C are (relative to SEQ ID NO:17): E125, L126, and G127. Preferred sites for cysteine substitutions in the last 3 amino acids of helix C are (relative to SEQ ID NO:17): 5145, R146, and L147. Preferred sites for cysteine substitutions in the first 3 amino acids of helix D are (relative to SEQ ID NO:17): A173, A174, and H175. Preferred sites for cysteine substitutions in the last 3 amino acids of helix D are (relative to SEQ ID NO:17): L194, L195, and K196.

As used herein, reference to an isolated protein or polypeptide in the present invention, including an IL-11 protein described particularly herein, includes full-length proteins, fusion proteins, or any fragment (truncated form) or homologue of such a protein. Such a protein can include, but is not limited to, purified proteins, recombinantly produced proteins, membrane bound proteins, proteins complexed with lipids, soluble proteins and isolated proteins associated with other proteins. More specifically, an isolated protein according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. In addition, and again by way of example, a "human IL-11 protein" or a protein "derived from" a human IL-11 protein refers to a IL-11 protein (generally including a homologue of a naturally occurring IL-11 protein) from a human (*Homo sapiens*) or to a IL-11 protein that has been otherwise produced from the knowledge of the structure (e.g., sequence) and perhaps the function of a naturally occurring IL-11 protein from *Homo sapiens*. In other words, a human IL-11 protein includes any IL-11 protein that has substantially similar structure and function of a naturally occurring IL-11 protein from *Homo sapiens* or that is a biologically active (i.e., has biological activity) homologue of a naturally occurring IL-11 protein from *Homo sapiens* as described in detail herein. As such, a human IL-11 protein can include purified, partially purified, recombinant, mutated/modified and synthetic proteins. According to the present invention, the terms "modification" and "mutation" can be used interchangeably, particularly with regard to the modifications/mutations to the amino acid sequence of protein (or nucleic acid sequences) described herein. An isolated protein useful as an antagonist or agonist according to the present invention can be isolated from its natural source, produced recombinantly or produced synthetically.

As used herein, the term "homologue" is used to refer to a protein or peptide which differs from a naturally occurring protein or peptide (i.e., the "prototype" or "wild-type" protein) by modifications, including minor modifications, to the naturally occurring protein or peptide, but which maintains the basic protein and side chain structure of the naturally occurring form. Such changes include, but are not limited to: changes in one or a few (i.e., 1, 2, 3, 4, 5, 6, 7, 8, 9 or 10) amino acid side chains; changes one or a few amino acids, including deletions (e.g., a truncated form of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have either enhanced, decreased, or substantially similar properties as compared to the naturally occurring protein or peptide. A homologue can include an agonist of a protein or an antagonist of a protein. A cysteine variant of IL-11 is a homologue of IL-11.

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

In one embodiment, a homologue of a given protein comprises, consists essentially of, or consists of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homologue comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
   Reward for match=1
   Penalty for mismatch=−2
   Open gap (5) and extension gap (2) penalties
   gap x_dropoff (50) expect (10) word size (11) filter (on)
   For blastp, using 0 BLOSUM62 matrix:

Open gap (11) and extension gap (1) penalties
gap x_dropoff (50) expect (10) word size (3) filter (on).

According to the present invention, an isolated IL-11 protein, including a biologically active homologue or fragment thereof, has at least one characteristic of biological activity of activity the wild-type, or naturally occurring IL-11 protein (which can vary depending on whether the homologue or fragment is an agonist or antagonist of the protein, or whether an agonist or antagonist mimetic of the protein is described). In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Modifications, activities or interactions which result in a decrease in protein expression or a decrease in the activity of the protein, can be referred to as inactivation (complete or partial), down-regulation, reduced action, or decreased action or activity of a protein. Similarly, modifications, activities or interactions which result in an increase in protein expression or an increase in the activity of the protein, can be referred to as amplification, overproduction, activation, enhancement, up-regulation or increased action of a protein. The biological activity of an IL-11 protein according to the invention can be measured or evaluated using any assay for the biological activity of the protein as known in the art. Such assays are known in the art, and assays for IL-11 activity are described in the Examples.

In accordance with the present invention, an isolated polynucleotide (also referred to as an isolated nucleic acid molecule) is a nucleic acid molecule that has been removed from its natural milieu (e.g., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. A polynucleotide useful in the present invention can include a portion of a nucleic acid sequence (sense or non-sense strand) that is suitable for use as a hybridization probe or PCR primer for the identification of a full-length gene (or portion thereof), or to encode a protein or fragment (truncated form) or homologue thereof. An isolated nucleic acid molecule that includes a gene is not a fragment of a chromosome that includes such gene, but rather includes the coding region and regulatory regions associated with the gene, but no additional genes naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. Preferably, an isolated nucleic acid molecule of the present invention is produced using recombinant DNA technology (e.g., polymerase chain reaction (PCR) amplification, cloning) or chemical synthesis.

The minimum size of a nucleic acid molecule or polynucleotide of the present invention is a size sufficient to encode a protein having a desired biological activity, or sufficient to form a probe or oligonucleotide primer that is capable of forming a stable hybrid with the complementary sequence of a nucleic acid molecule encoding the natural protein (e.g., under moderate, high or very high stringency conditions). If the polynucleotide is an oligonucleotide probe or primer, the size of the polynucleotide can be dependent on nucleic acid composition and percent homology or identity between the nucleic acid molecule and a complementary sequence as well as upon hybridization conditions per se (e.g., temperature, salt concentration, and formamide concentration). The minimum size of a polynucleotide that is used as an oligonucleotide probe or primer is at least about 5 nucleotides in length, and preferably ranges from about 5 to about 50 or about 500 nucleotides or greater, including any length in between, in whole number increments (i.e., 5, 6, 7, 8, 9, 10, . . . 33, 34, . . . 256, 257, . . . 500). There is no limit, other than a practical limit, on the maximal size of a nucleic acid molecule of the present invention, in that the nucleic acid molecule can include a portion of a protein-encoding sequence or a nucleic acid sequence encoding a full-length protein.

As used herein, stringent hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na+) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

In one embodiment of the present invention, any of the amino acid sequences described herein, including homologues of such sequences (e.g., cysteine muteins), can be produced with from at least one, and up to about 20, additional heterologous amino acids flanking each of the C- and/or N-terminal end of the given amino acid sequence. The resulting protein or polypeptide can be referred to as "consisting essentially of" a given amino acid sequence. According to the present invention, the heterologous amino acids are a sequence of amino acids that are not naturally found (i.e., not found in nature, in vivo) flanking the given amino acid sequence or which would not be encoded by the nucleotides that flank the naturally occurring nucleic acid sequence encoding the given amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a given amino acid sequence that can be flanked by from at least one, and up to as many as about 60, additional heterologous nucleotides at each of the 5' and/or the 3' end of the nucleic acid sequence encoding the given amino acid sequence. The heterologous nucleotides are not naturally found (i.e., not found in nature, in vivo) flanking the nucleic acid sequence encoding the given amino acid sequence as it occurs in the natural gene.

One embodiment of the present invention relates to a method to produce a cysteine mutein of IL-11, including any cystein mutein of IL-11 described herein. Such a method includes the steps of production and purification of the IL-11 mutein using an insect system as described in detail any of Examples 2-4, using an *E. coli* system as described in detail in Examples 7-8, or using an *E. coli* intein system as described in detail Example 9.

One embodiment of the present invention relates to stimulating production of platelets in an animal, comprising administering to the animal an interleukin-11 (IL-11) cysteine mutein as described herein, or a composition comprising such a cysteine mutein, and in one embodiment, as prepared using methods described herein (see Examples) or alternatively, as described in PCT Publication No. WO 01/87925, published Nov. 22, 2001, or in PCT Publication No. WO 00/42175, published Jul. 20, 2000, each of which is incorporated herein by reference in its entirety.

One embodiment of the invention relates to a method to treat or protect an animal from a disease or condition that is amenable to treatment with interleukin-11 (IL-11), comprising administering to the animal a composition comprising an IL-11 cysteine mutein as described herein. In one embodiment, the cysteine mutein is prepared using methods described herein or in PCT Publication No. WO 01/87925 or in PCT Publication No. WO 00/42175, supra.

Another embodiment of the invention relates to a method to prevent or treat the occurrence of thrombocytopenia in an animal comprising administering to the animal a composition comprising an IL-11 cysteine mutein as described herein and in one embodiment, as prepared using methods described herein or in PCT Publication No. WO 01/87925 or in PCT Publication No. WO 00/42175, supra. In a preferred aspect of the invention, administration of the IL-11 cysteine mutein accelerates recovery from thrombocytopenia and/or reduces the severity of thrombocytopenia in the patient. The thrombocytopenia to be prevented or treated using this method can include, but is not limited to: (a) thrombocytopenia resulting from myelosuppressive chemotherapy; (b) thrombocytopenia resulting from other chemical treatments; (c) thrombocytopenia resulting from radiological treatments; (d) thrombocytopenia resulting from disease; (e) thrombocytopenia resulting from idiopathic causes; (f) thrombocytopenia resulting from drug treatments, including interferons and ribavarin; (g) thrombocytopenia in neonates; (h) thrombocytopenia resulting from myelodysplastic syndromes; (i) thrombocytopenia resulting from aplastic anemia; and (j) thrombocytopenia resulting from cirrhosis.

Approximately 1.4 million people receive myelosuppressive chemotherapy each year in the U.S. Thrombocytopenia is one of the most common hematological complications of chemotherapy (occurs in 40-60% of patients) and can lead to dose reductions or delays in chemotherapy, which reduce effectiveness of the chemotherapy treatment and adversely affect patient survival (reviewed in Cairo, 2000). Thrombocytopenia is a common problem in other disease indications besides cancer. For example, thrombocytopenia is the most common hematological abnormality seen in neonates (reviewed in Ramasethu, 2004). Thrombocytopenia is a major complication of PEGylated interferon/ribavarin treatments in patients with Hepatitis C, and can lead to dose-reductions or delays in anti-viral therapy, which can adversely affect treatment outcome (Dieterich and Spivak, 2003). A subset of patients with bone marrow disorders such as myelodysplastic syndromes and aplastic anemia respond to IL-11 therapy by reversing their thrombocytopenia (Gordon, 1999; Kurzrock et al., 2001; Tsimberidou et al., 2005). IL-11 also is effective at reversing thrombocytopenia in patients with cirrhosis (Ghalib et al., 2003). Thus, there are many potential clinical settings where a composition comprising an IL-11 cysteine mutein as described herein will prove useful.

IL-11, like many cytokines, has a short circulating half-life, which necessitates daily subcutaneous injections for maximum effectiveness in humans. The present inventors have created novel IL-11 analogs (e.g., the IL-11 cysteine muteins described herein) with improved in vivo characteristics such as increased circulating half-life and improved therapeutic efficacy through site-specific chemical modification of the protein with Polyethylene Glycol (PEG) reagents (e.g., using cysteine-reactive PEGylation and/or by PEGylation of other residues in the protein). Many of these analogs were created by introducing a "free" cysteine residue (i.e., a cysteine residue not involved in a disulfide bond) into the protein using site-directed mutagenesis. The free cysteine residue(s) serve as the site for covalent modification of the protein with cysteine-reactive PEG reagents. The present invention teaches a variety of human IL-11 cysteine muteins that can be modified with cysteine-reactive PEG reagents and retain biological activity, and the Examples section below describes additional methods of preparing such muteins.

Human and rodent IL-11 proteins perform similar functions in their respective species and studies with rodent IL-11 proteins can be used to predict the function of human IL-11 in humans. Human and rodent IL-11 proteins share about 69% amino acid identity, and have cross-species cross-reactivity in terms of biological activity and receptor binding. Indeed, the Examples below demonstrate the use of a human IL-11 cysteine mutein in in vivo studies using rats. It is possible to use the amino acid identity between human and rodent IL-11 proteins to construct human IL-11 cysteine muteins that can be expressed, purified and PEGylated using procedures described herein, and the biological activities of the PEGylated IL-11 cysteine muteins can be tested in rodent animal disease models and used to predict the effectiveness of PEGylated human IL-11 cysteine variants in humans. Similarly, one can construct rodent analogs of human IL-11 cysteine variants to be used in rodent animal disease models and again predict the effectiveness of corresponding or equivalent PEGylated human cysteine variants.

A preferred embodiment of the present invention is a PEGylated IL-11 protein. A more preferred embodiment is a monoPEGylated IL-11 protein. MonoPEGylated indicates that the protein is modified with a single PEG (i.e., at a single site in the protein). It is well known in the art that PEGylated proteins can have widely varying in vitro bioactivities due to where the PEG attaches to the protein. A preferred composition of the present invention is a PEGylated or monoPEGylated IL-11 analog that has in vitro bioactivity ($EC_{50}$s) of less than about 1000 ng/mL in an IL-11 dependent in vitro bioassay. The preferred IL-11-dependent bioassay is the IL-11-dependent cell proliferation bioassay using B9-11 cells, described herein. A more preferred composition is a PEGylated or monoPEGylated IL-11 analog with an $EC_{50}$ of less than about 100 ng/mL in an in vitro bioassay. An even more preferred composition is a PEGylated or monoPEGylated IL-11 protein with an $EC_{50}$ less than about 20 ng/mL in an in vitro bioassay. The Examples presented below teach preferred methods for preparing PEGylated and monoPEGylated IL-11 analogs that have the in vitro bioactivities described above.

Toward that end, the present inventors have constructed multiple IL-11 cysteine muteins, as discussed above, and have and tested the human IL-11 *200C mutein in in vivo assays for IL-11 activity. As shown in the Examples, the PEGylated human IL-11 cysteine variant is effective at stimulating platelet production in a mammal (a rodent), which indicates that PEGylated human IL-11 cysteine muteins will be effective at stimulating platelet production in humans. Stimulating platelet production will be useful for ameliorating disease indications in which such activity is impaired, such as thrombocytopenia. Indeed, the PEGylated IL-11 cysteine variant was further shown (see Examples) to accelerate recovery and reduce the severity of thrombocytopenia in a rat animal model. In the rat model, the thrombocytopenia was induced by myelosuppression, but the present invention is useful for treating thrombocytopenia resulting from any cause (chemical, radiological, disease, etc.). In addition, the Examples demonstrate that the IL-11 cysteine variants of the invention have a superior half-life as compared to the wild-type protein, may have better activity than the wild-type protein, and may have in vivo efficacy after a single injection, where a single injection of wild-type IL-11 had no detectable effect in vivo. The other cysteine variants described in the Examples are similarly expected to be useful in in vivo methods according to the invention.

As discussed above, various embodiments of the invention relate to methods of use of IL-11 cysteine muteins. In particular, the present invention relates to the use of these muteins to protect an animal from a disease or condition that is amenable to treatment by the use of wild-type IL-11, or which might be particularly amenable to treatment using the IL-11 cysteine muteins of the present invention.

As used herein, the phrase "protected from a disease" refers to reducing the symptoms of the disease, reducing the occurrence of the disease, and/or reducing the severity of the disease. Protecting an animal can refer to the ability of a therapeutic composition of the present invention, when administered to an animal, to prevent a disease from occurring and/or to cure or to alleviate disease symptoms, signs or causes. As such, to protect an animal from a disease includes both preventing disease occurrence (prophylactic treatment) and treating an animal that has a disease or that is experiencing initial symptoms of a disease (therapeutic treatment). In particular, protecting an animal from a disease is accomplished by inducing a beneficial or protective therapeutic response in the animal by administration of an IL-11 cysteine mutein, or any of the other cysteine muteins of the present invention as described herein. The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

Accordingly, an IL-11 cysteine mutein of the present invention can be administered to regulate the stimulation of platelet production in an animal. An IL-11 cysteine mutein can be administered to an animal to prevent or ameliorate any disease or condition for which the use of the wild-type protein can be used. Such diseases and conditions are described in detail above. In one embodiment, an IL-11 cysteine mutein of the present invention is used to protect or treat an animal that has or is at risk of developing thrombocytopenia, and specifically accelerates the recovery from thrombocytopenia and/or reduces the severity of the thrombocytopenia in the animal.

An IL-11 cysteine mutein or composition comprising the same of the present invention is administered to an animal in a manner effective to deliver the composition to a target cell, a target tissue, or systemically to the animal, whereby provision of a therapeutic benefit is achieved as a result of the administration of the mutein or composition. Suitable administration protocols include any in vivo or ex vivo administration protocol. According to the present invention, suitable methods of administering a composition of the present invention to a patient include any route of in vivo administration that is suitable for delivering the composition into a patient. The preferred routes of administration will be apparent to those of skill in the art, depending on the type of condition to be prevented or treated and/or the target cell population.

Cysteine muteins of the present invention are preferably administered in a composition. Compositions can include a cysteine mutein of the invention and any other suitable pharmaceutically acceptable carrier, as well as, in some aspects, additional components that may be useful in the treatment of a give disease or condition. According to the present invention, a "pharmaceutically acceptable carrier" includes pharmaceutically acceptable excipients and/or pharmaceutically acceptable delivery vehicles, which are suitable for use in administration of the composition to a suitable in vitro, ex vivo or in vivo site. A suitable in vitro, in vivo or ex vivo site is preferably any site where the cysteine mutein will provide a detectable effect as compared to in the absence of the mutein, and includes a disease site or a site of cell types to be contacted with the mutein. Preferred pharmaceutically acceptable carriers are capable of maintaining the mutein of the present invention in a form that, upon arrival of the mutein at the cell target in a culture or in patient, the mutein is capable of interacting with its target (e.g., platelets or progenitor cells thereof).

Suitable excipients of the present invention include excipients or formularies that transport or help transport, but do not specifically target a composition to a cell or area (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Compositions of the present invention can be sterilized by conventional methods and/or lyophilized One type of pharmaceutically acceptable carrier includes a controlled release formulation that is capable of slowly releasing a composition of the present invention into a patient or culture. As used herein, a controlled release formulation comprises a cysteine mutein of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other carriers of the present invention include liquids that, upon administration to a patient, form a solid or a gel in situ. Preferred carriers are also biodegradable (i.e., bioerodible). In the event that a cysteine mutein of the invention is administered as a recombinant nucleic acid molecule encoding the cysteine mutein (e.g., gene therapy or genetic immunization), suitable carriers include, but are not limited to liposomes, viral vectors or other carriers, including ribozymes, gold particles, poly-L-lysine/DNA-molecular conjugates, and artificial chromosomes. Natural lipid-containing carriers include cells and cellular membranes. Artificial lipid-containing carriers include liposomes and micelles.

A carrier of the present invention can be modified to target to a particular site in a patient, thereby targeting and making use of a compound of the present invention at that site. A pharmaceutically acceptable carrier which is capable of targeting can also be referred to herein as a "delivery vehicle" or "targeting carrier". Suitable modifications include manipulating the chemical formula of the lipid portion of the delivery vehicle and/or introducing into the vehicle a targeting agent capable of specifically targeting a delivery vehicle to a preferred site or target site, for example, a preferred cell type. A "target site" refers to a site in a patient to which one desires to deliver a composition. Suitable targeting compounds include ligands capable of selectively (i.e., specifically) binding another molecule at a particular site. Examples of such ligands include antibodies, antigens, receptors and receptor ligands. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

One delivery vehicle of the present invention is a liposome. A liposome is capable of remaining stable in an animal for a sufficient amount of time to deliver a nucleic acid molecule or protein described in the present invention to a preferred site in the animal. A liposome, according to the present invention, comprises a lipid composition that is capable of delivering a nucleic acid molecule or protein to a particular, or selected, site in a patient. A liposome according to the present invention comprises a lipid composition that is capable of fusing with the plasma membrane of the targeted cell to deliver a nucleic acid molecule or protein into a cell. Suitable liposomes for use with the present invention include any liposome. Preferred liposomes of the present invention include those liposomes commonly used in, for example, gene delivery methods known to those of skill in the art. More preferred liposomes comprise liposomes having a polycationic lipid composition and/or liposomes having a cholesterol backbone conjugated to polyethylene glycol. Complexing a liposome with a nucleic acid molecule or protein of the present invention can be achieved using methods standard in the art.

Another type of delivery vehicle, when the cysteine mutein is administered as a nucleic acid encoding the mutein, comprises a viral vector. A viral vector includes an isolated nucleic acid molecule, in which the nucleic acid molecules are packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

According to the present invention, an effective administration protocol (i.e., administering a therapeutic composition in an effective manner) comprises suitable dose parameters and modes of administration that result in the desired effect in the patient (e.g., stimulation of platelet production), preferably so that the patient is protected from the disease (e.g., by disease prevention or by alleviating one or more symptoms of ongoing disease). Effective dose parameters can be determined using methods standard in the art for a particular disease. Such methods include, for example, determination of survival rates, side effects (i.e., toxicity) and progression or regression of disease.

In accordance with the present invention, a suitable single dose size is a dose that results in the desired therapeutic effect in the patient, depending on the cysteine mutein that is administered, or in the amelioration of at least one symptom of a condition in the patient, when administered one or more times over a suitable time period. Doses can vary depending upon the disease being treated. One of skill in the art can readily determine appropriate single dose sizes for a given patient based on the size of a patient and the route of administration.

In one aspect of the invention, a suitable single dose of a therapeutic composition of the present invention is an amount that, when administered by any route of administration, provides a therapeutic effect in the patient as described above, as compared to a patient which has not been administered with the therapeutic composition of the present invention (i.e., a control patient), as compared to the patient prior to administration of the composition, or as compared to a standard established for the particular disease, patient type and composition.

In one aspect of the invention an appropriate single dose of a cysteine mutein of the present invention is at least about 0.01 micrograms per kg of the animal to which the mutein is administered, and in other aspects, at least about 0.1 micrograms/kg, at least about 0.2 micrograms/kg, at least about 0.5 micrograms/kg, at least about 1 micrograms/kg, at least about 5 micrograms/kg, at least about 10 micrograms/kg, at least about 25 micrograms/kg, at least about 50 micrograms/kg, at least about 75 micrograms/kg, at least about 100 micrograms/kg, at least about 200 micrograms/kg, at least about 300 micrograms/kg, at least about 400 micrograms/kg, at least about 500 micrograms/kg, at least about 750 micrograms/kg, at least about 1 mg/kg, or at least about 5 mg/kg.

As discussed above, a therapeutic composition of the present invention is administered to a patient in a manner effective to deliver the composition to a cell, a tissue, and/or systemically to the patient, whereby the desired result is achieved as a result of the administration of the composition. Suitable administration protocols include any in vivo or ex vivo administration protocol. The preferred routes of administration will be apparent to those of skill in the art, depending on the type of condition to be prevented or treated; whether the composition is nucleic acid based or protein based; and/or the target cell/tissue. For proteins or nucleic acid molecules, preferred methods of in vivo administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, intranasal, oral, bronchial, rectal, topical, vaginal, urethral, pulmonary administration, impregnation of a catheter, and direct injection into a tissue. Routes useful for deliver to mucosal tissues include, bronchial, intradermal, intramuscular, intranasal, other inhalatory, rectal, subcutaneous, topical, transdermal, vaginal and urethral routes. Combinations of routes of delivery can be used and in some instances, may enhance the therapeutic effects of the composition. Particularly preferred routes of delivery include subcutaneous and intravenous delivery.

Ex vivo administration refers to performing part of the regulatory step outside of the patient, such as administering a composition of the present invention to a population of cells removed from a patient under conditions such that the composition contacts and/or enters the cell, and returning the cells to the patient. Ex vivo methods are particularly suitable when the target cell type can easily be removed from and returned to the patient.

Many of the above-described routes of administration, including intravenous, intraperitoneal, intradermal, and intramuscular administrations can be performed using methods standard in the art. Aerosol (inhalation) delivery can also be performed using methods standard in the art (see, for example, Stribling et al., Proc. Natl. Acad. Sci. USA 189: 11277-11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers include plastic capsules or tablets such as those known in the art.

One method of local administration is by direct injection. Direct injection techniques are particularly useful for administering a composition to a cell or tissue that is accessible by surgery, and particularly, on or near the surface of the body. Administration of a composition locally within the area of a target cell refers to injecting the composition centimeters and preferably, millimeters from the target cell or tissue.

Various methods of administration and delivery vehicles disclosed herein have been shown to be effective for delivery of a nucleic acid molecule to a target cell, whereby the nucleic acid molecule transfected the cell and was expressed. In many studies, successful delivery and expression of a heterologous gene was achieved in preferred cell types and/or using preferred delivery vehicles and routes of administration of the present invention.

In the method of the present invention, compositions can be administered to any animal and preferably, to any member of the Vertebrate class, Mammalia, including, without limitation, primates, rodents, livestock and domestic pets. Livestock include mammals to be consumed or that produce useful products (e.g., sheep for wool production). Preferred mammals to protect include humans, dogs, cats, mice, rats, sheep, cattle, horses and pigs, with humans being particularly preferred.

The following examples are provided to demonstrate how the "rules" described herein can be used to create cysteine-added variants of IL-11. The examples also demonstrate the therapeutic uses of cysteine variants of the present invention. The examples are not intended to be limiting, but only exemplary of specific embodiments of the invention.

EXAMPLES

Example 1

Cloning of IL-11

IL-11 is a pleiotropic cytokine that stimulates hematopoiesis, lymphopoeisis and acute phase responses. IL-11 shares many biological effects with IL-6. The amino acid sequence of human IL-11 (SEQ ID NO:17) is given in Kawashima et al. (1991) and Paul et al. (1990) both incorporated herein by reference. IL-11 is synthesized as a precursor protein of 199 amino acids that is cleaved to yield a mature protein of 178 amino acids. There are no N-linked glycosylation sites in the protein. IL-11 has four major alpha helices referred to as helices A-D. Relative to the amino acid sequence shown in SEQ ID NO:17, helix A encompasses amino acids 37-56, helix B encompasses amino acids 92-112, helix C encompasses amino acids 125-147 and helix D encompasses amino acids 173-196 Amino acids 1-21 of SEQ ID NO:17 encompass the IL-11 signal sequence.

This invention provides cysteine-added variants of IL-11, wherein cysteine substitutions or insertions are made in one or more of the region proximal to the A helix (amino acids 22-36 of SEQ ID NO:17), distal to the D helix (amino acids 197-199 of SEQ ID NO:17), in the A-B loop (amino acids 57-91 of SEQ ID NO:17), in the B-C loop (amino acids 113-124 of SEQ ID NO: 17), and in the C-D loop (amino acids 148-172 of SEQ ID NO:17). This invention also provides cysteine-added variants at the first three or last three amino acids in any one or more of helices A, B, C and D. Variants in which cysteine residues are added proximal to the first amino acid of the mature protein (amino acid 22 of SEQ ID NO:17) or distal to the final amino acid of the mature protein (amino acid 199 of SEQ ID NO:17) also are provided.

Preferred site for cysteine substitutions in the region preceding helix A of IL-11 are: P22, G23, P24, P25, P26, G27, P28, P29, R30, V31, S32, P33, D34, P35, and R36. Preferred sites for cysteine substitutions in the A-B loop of IL-11 are: A57, A58, Q59, L60, R61, D62, K63, F64, P65, A66, D67, G68, D69, H70, N71, L72, D73, S74, L75, P76, T77, L78, A79, M80, S81, A82, G83, A84, L85, G86, A87, L88, Q89, L90, and P91. Preferred sites for cysteine substitutions in the C-D loop of IL-11 are: A148, L149, P150, Q151, P152, P153, P154, D155, P156, P157, A158, P159, P160, L161, A162, P163, P164, S165, 5166, A167, W168, G169, G170, I171, and R172. Preferred sites for cysteine substitutions in region following helix D of IL-11 are: T197, R198, and L199. Preferred sites for cysteine substitutions in the first 3 amino acids of helix A are: A37, D38, and L39. Preferred sites for cysteine substitutions in the last 3 amino acids of helix A are: R54, Q55, and L56. Preferred sites for cysteine substitutions in the first 3 amino acids of helix B are: G92, V93, and L94. Preferred sites for cysteine substitutions in the last 3 amino acids of helix B are: W110, L111, and R112. Preferred sites for cysteine substitutions in the first 3 amino acids of helix C are: E125, L126, and G127. Preferred sites for cysteine substitutions in the last 3 amino acids of helix C are: 5145, R146, and L147. Preferred sites for cysteine substitutions in the first 3 amino acids of helix D are: A173, A174, and H175. Preferred sites for cysteine substitutions in the last 3 amino acids of helix D are: L194, L195, and K196.

A full-length cDNA encoding IL-11 was amplified by PCR as two segments which were then subsequently spliced together to generate the full length clone by the technique of "overlap extension" (Horton et al., 1993). One segment, encoding amino acids 1 through 147, was amplified by PCR from single-stranded cDNA derived from total RNA extracted from the human bladder carcinoma cell line 5637 (American Type Culture Collection, Rockville, Md.). A PCR reaction using the products of the first strand synthesis as template was carried out with forward primer BB265 (5>CG-CAAGCTTGCCACCATGAACTG TGTTTGCCGC-CTG>3; SEQ ID NO:42) and reverse primer BB273 (5>GCGGGACATCAGGAG CTGCAGCCGGCGCAG>3; SEQ ID NO:43). Primer BB265 anneals to the 5' end of the coding sequence for the IL-11 secretory signal sequence and the reverse primer, BB273, anneals to sequence encoding amino acids 138-147 and spans the junction of exons 4 and 5 (McKinley et al., 1992). The ~450 bp product of this reaction was gel-purified and used in subsequent splicing reactions. The second segment, containing DNA sequences encoding amino acids 142 through 197, was amplified by PCR from human genomic DNA (STRATAGENE, San Diego, Calif.). A PCR reaction using human genomic DNA as template was carried out with forward primer BB272 (5>CAGCTCCT-GATGTCCCGCCTGGCCCTG>3; SEQ ID NO:44) and reverse primer BB274 (5>AGTCTTCAGCAGCAGCAGTC-CCCTCAC>3; SEQ ID NO:45). BB272 anneals to sequences encoding amino acids 142-150 and spans the junction of exons 4 and 5. BB274 anneals to sequence encoding amino acids 189-197. The ~170 bp product of this reaction was gel-purified and used in subsequent splicing reactions.

The gel purified ~450 bp and ~170 bp products were spliced together in a PCR reaction which included the ~450 bp and ~170 bp products as template and forward primer BB265 (described above) and reverse primer BB275 (5>CGCGGATCCTCCGACAGCCGAGTCT-TCAGCAGCAG>3; SEQ ID NO:46). BB275 anneals to the DNA sequence encoding amino acids 191-199. The ~620 bp product of this reaction was gel-purified, digested with HindIII and Bam HI and cloned into pcDNA3.1(+) vector (Invitrogen Corporation, Carlsbad, Calif.) that had been digested with Hind III and Bam HI, alkaline phosphatase treated, and gel purified. A clone with the correct DNA sequence was designated pcDNA3.1(+)::IL-11fus or pBBT298.

Example 2

Expression of IL-11 in Insect Cells

IL-11 was expressed in insect cells and secreted using the IL-11 signal sequence present in the cDNA clone. For insect cell expression, the cloned IL-11 cDNA of pBBT298 was modified at both the 5' and 3' ends to create a "flag-tagged" IL-11 cDNA. At the 5' end, the sequence CAAA was added immediately upstream of the initiator ATG to enhance translation. This sequence comprises a proposed consensus translational initiation sequence for baculovirus (Ranjan and Hasnain, 1995). At the 3' end, DNA encoding the 8 amino acid FLAG sequence (asp-tyr-lys-asp-asp-asp-asp-lys; SEQ ID NO:47), preceded by a flexible linker encoding the sequence: ser-gly-gly-ser-gly-gly-ser (SEQ ID NO:48), was added following amino acid 199 to provide a simple purification system. DNA encoding the FLAG epitope was fused to the IL-11 gene. These modifications were made via PCR using oligonucleotide primers that incorporated the desired additions to the IL-11 sequence and the DNA sequence of this construct was confirmed. For expression in baculovirus, the "FLAG-tagged" IL-11 cDNA was cloned into the baculovirus transfer vector pBlueBac4.5 (Invitrogen). Purified plasmid DNAs were used to cotransfect *Spodoptera frugiperda* derived insect cell line Sf9 along with linearized (Bsu36 I digested) Bac-N-Blue™ (Invitrogen) baculovirus DNA. The co-transfection was performed according to the Invitrogen "Bac-N-Blue™ Transfection Kit" protocols using $2\times10^6$ Sf 9 cells to generate a ~2 ml supernatant. Dilutions of this supernatant were assayed on Sf 9 cells at 27° C. for plaque formation. Ten plaques were picked and each plaque was used to inoculate $2.5\times10^6$ Sf 9 cells in a T25 flask containing 5 ml of Grace's Insect Media supplemented with 10% fetal bovine serum (FBS). After 5 days the supernatants from these infected cells (the "P1" stocks) were collected and six supernatants were tested by Western Blot for IL-11 expression using a polyclonal anti-IL-11 antisera obtained from R&D Systems, Inc. Alkaline phosphatase conjugated rabbit anti-goat IgG1 (Pierce Chemical company) was used as the secondary antibody. Western blots were developed using a NBT/BCIP development substrate (Promega Corporation, Madison, Wis.). We also constructed an IL-11 mutein in which P22, the first amino acid of the mature protein, is deleted (referred to as del P22). The del P22 mutant was expressed in insect cells using similar procedures. Several plaques for both wild type IL-11 and the del P22 mutant were positive for IL-11 protein expression, as judged by Western blot. One positive supernatant for each protein was tested in the in vitro IL-11 bioassay described in Example 3. Both supernatants stimulated proliferation of the IL-11-dependent cell line in a dose-dependent manner, indicating that they contained biologically active IL-11 protein.

Example 3

Construction, Expression and Purification of IL-11 Cysteine Muteins from Insect Cells This example provides cysteine variants of IL-11. The novel IL-11-derived molecules of this example can be formulated and tested for activity essentially as set forth in Example 2 above for wild-type IL-11.

IL-11 muteins containing a single cysteine substitution were constructed in the wild type human IL-11 sequence. The IL-11 cysteine muteins were expressed in insect cells as described in Example 2. The IL-11 amino acid sequence is shown in SEQ ID NO:17 of PCT Publication No. WO 99/03887, incorporated herein by reference in its entirety, which represents the amino acid sequence of the 199 amino acid precursor protein, wherein amino acids 1-21 comprise the IL-11 signal sequence and are not present in the mature IL-11 protein. The following cysteine substitution muteins were constructed by site-directed mutagenesis and are numbered according to SEQ ID NO:17: P22C, G23C, P24C, G27C, Q151C, A158C and A162C. In addition, the inventors constructed a cysteine mutein in which a cysteine residue was added to the carboxy-terminus of the protein, i.e., immediately following amino acid 199. This mutein was termed *200C.

The P22C, G23C, P24C, G27C, Q151C, A158C, A162C and *200C muteins were expressed in insect cells as described in Example 2. Muteins P22C, G23C, P24C, G27C, A162C and *200C were tested for biological activity versus a wild type IL-11 control in an in vitro cell-line based proliferation assay. IL-11 control proteins were IL-11 prepared by us and an IL-11 protein obtained from R&D Systems, Inc. Supernatants of baculovirus infected insect cell lysates were tested in the bioassay, and the IL-11 cysteine mutein or wild type IL-11 protein present in the lysate was quantitated by a commercially available (R & D Systems) IL-11 ELISA assay. The bioassay measures IL-11-stimulated proliferation of a derivative the B9 cell line that has been adapted to proliferate in response to IL-11. The mouse B9 hybridoma cell line was obtained from the German Collection of Microorganisms and Cell Cultures (DSMZ). The B9 line was passaged in IL-11 to select for a line that proliferates in response to IL-11 (referred to as B9-11 cells).

B9-11 cells were maintained in RPMI 1640 media supplemented with 10% FBS, 50 units/ml penicillin, 50 µg/ml streptomycin, 50 µM beta mercaptoethanol and 50 ng/ml recombinant human IL-11 (R&D Systems, Inc.). For bioassays, B9-11 cells were washed and resuspended at a concentration of $1 \times 10^5$/ml in cell maintenance media minus IL-11. Fifty µl ($5 \times 10^3$ cells) of the cell suspension was aliquotted per test well of a flat bottom 96 well tissue culture plate. Serial 3-fold dilutions of the protein samples were prepared in maintenance media minus IL-11. Serial dilutions of recombinant human IL-11 (R&D Systems, Inc.) were analyzed in parallel. Fifty µl of the diluted protein samples were added to the test wells and the plates incubated at 37° C. in a humidified 5% $CO_2$ tissue culture incubator. Protein samples were assayed in triplicate wells. After three days, 20 µl of CellTiter 96 AQueous One Solution (Promega Corporation, Madison, Wis.) was added to each well and the plates incubated at 37° C. in the tissue culture incubator for 1-4 h. Absorbance of the wells was read at 490 nm using a microplate reader. Control wells contained media but no cells. Mean absorbance values for the triplicate control wells were subtracted from mean values obtained for the test wells.

In this assay, all of the IL-11 cysteine muteins tested were biologically active, as measured by their ability to stimulate proliferation of B9-11 cells. The $EC_{50}$ (the concentration of protein resulting in one half the maximal stimulation of proliferation) of the muteins ranged from indistinguishable from the $EC_{50}$ of the wild type IL-11 control to within approximately 2-fold of the $EC_{50}$ of the wild type control. $EC_{50}$s are shown in Table 1.

TABLE 1

In vitro bioactivities of insect cell-expressed IL-11 and IL-11 cysteine muteins.

| IL-11 Protein | $EC_{50}$ (ng/ml) |
| --- | --- |
| Wild type IL-11 (R&D Systems, Inc.) | 3.0 |
| Wild type IL-11 (Bolder BioTechnology) | 4.2 |
| del P22 | 5.9 |
| P22C | 3.3 |
| G23C | 3.4 |
| P24C | 3.3 |
| G27C | 3.4 |
| A162C | 5.0 |
| *200C | 2.8 |

Example 4

Preparation and Purification of PEGylated IL-11 Cysteine Muteins From Insect Cells Wild type IL-11 and three IL-11 cysteine muteins (P24C, A162C and *200C) were purified to homogeneity from the supernatants of baculovirus infected insect cell lysates. A positive supernatant for each isolate was used to prepare a 500 ml high titer viral stock by inoculating a 500 ml spinner flask culture of Sf 9 cells in Grace's Insect Media supplemented with 10% FBS. The cells were grown at 27° C. The supernatants from these cultures were harvested after 7 days and found to have titers of ~$10^8$ plaque-forming-units/ml. These amplified viral stocks were subsequently used to infect 500 ml cultures for larger scale production of wild type IL-11 and the cysteine muteins. 500 ml cultures of Sf 9 cells in Grace's Insect Media supplemented with 10% FBS were grown in a spinner flasks to a titer of $1.0 \times 10^6$/ml and then infected with viruses at a multiplicity of infection of 1. After 3 days the supernatants from these cultures were clarified by centrifugation and filtered through a 0.21 µM filter. The IL-11 proteins were purified in a single step procedure using Anti-FLAG M2 Affinity Gel (Sigma). The affinity gel was washed with 3 column volumes of 0.1M glycine, pH 3.0, 0.02% Tween 20 and 10% glycerol, then equilibrated with 5 column volumes of 50 mM Tris pH 7.5, 150 mM NaCl, 0.02% Tween 20 and 10% glycerol. For wild type IL-11 the clarified baculoviral cell supernatant was adjusted to 150 mM NaCl, and the equilibrated resin was added. For IL-11 cysteine muteins the clarified baculoviral cell supernatant was adjusted to 150 mM NaCl, 5 mM cystine and the equilibrated resin was added. Batch loading was done at 4° C. overnight on a roller bottle apparatus and the resin was recovered using a Pharmacia XK 16/20 FPLC column (GE Healthcare) and washed with Tris buffer until the A280 reached baseline. The bound protein was eluted with 0.1M glycine pH 3.0, 0.02% Tween 20, 10% glycerol and fractions were collected and neutralized with 1.0M Tris pH 9.0. Column fractions were prepared in SDS-PAGE sample buffer with the addition of 2% BME (beta-mercaptoethanol) when desirable and electrophoresed on precast 14% Tris-glycine polyacrylamide gels. The purified IL-11 cysteine muteins were predominantly monomeric. On non-reducing gels a small amount of dimeric material was observed in the purified cysteine muteins but not in purified wild type IL-11. Under reducing conditions only the monomer forms were observed, indicating that the dimer is formed through an intermolecular disulphide bond. The purified proteins were estimated to be greater than 90% pure by Coomassie Blue staining of SDS gels. The purified proteins were concentrated for subsequent experiments. Fractions from the anti-FLAG M2 affinity column that contained most of the IL-11 proteins were pooled and loaded onto a CM S Sepharose Fast Flow (GE Healthcare) column The bound protein was eluted with a 1 M NaCl bump.

PEGylation reactions included 200 µg of each protein, a 20× molar excess of 20 kDa PEG maleimide and a 20× molar excess of TCEP (Tris[2-carboxyethylphosphine]hydrochloride, Pierce Chemical Company). Reactions were performed at pH 8.0 at room temperature. Control experiments demonstrated that the IL-11 cysteine muteins needed to be reduced, at least partially, for efficient PEGylation. After 2 hours the PEGylation mixture was diluted 10× with 10 mM borate, pH 8.0, 10% glycerol, 0.02% Tween 20 (Buffer A) and loaded onto a 1 ml S-Sepharose column equilibrated in Buffer A. The column was washed with equilibration buffer and bound proteins eluted by a 1 M NaCl bump in 10 mM borate, pH 8.0, 10% glycerol, 0.02% Tween 20. This step served to concentrate the material prior to separation of PEGylated and unmodified forms via size exclusion chromatography. A Superdex 200 10/30 column was equilibrated with 50 mM NaPO$_4$ pH 7.5, 150 mM NaCl, 10% glycerol. After equilibration, a 0.5 ml sample containing the concentrated PEG-IL-11 cysteine muteins was loaded onto the sizing column and an isocratic gradient was run. Fractions containing PEGylated proteins were identified by SDS-PAGE.

SDS-PAGE analysis showed that the major early peak consisted of homogeneous monoPEGylated IL-11 cyteine mutein. Only monoPEGylated protein was detected, consistent with the muteins containing a single cysteine residue. Other later eluting fractions contained unreacted monomer and some dimeric material formed during the PEG reaction. PEGylation efficiencies for these muteins were 60% or greater, as estimated from the chromatographic trace of the sizing column run. Fractions containing the PEGylated cysteine muteins but no unmodified protein, were pooled, stored −80° C., and subsequently used in bioassays.

The purified cysteine muteins and the purified PEGylated cysteine muteins were assayed for biological activity vs. a wild type IL-11 control in the in vitro B9-11 cell-line proliferation assay. Protein concentrations were determined using human IL-11 ELISAs (R&D Systems, Inc.) and by Bradford analysis. All of the purified cysteine muteins and the purified PEGylated cysteine muteins were biologically active. The EC$_{50}$s of the purified cysteine muteins and the purified PEGylated cysteine muteins ranged from indistinguishable from the EC$_{50}$ of the wild type IL-11 control to within approximately 2-fold of the EC$_{50}$ of the wild type control. EC$_{50}$s of the proteins measured by ELISA were lower than the EC$_{50}$s measured by Bradford analysis.

TABLE 2

In vitro bioactivities of insect cell-expressed IL-11, IL-11 cysteine muteins and PEGylated IL-11 cysteine muteins.

| IL-11 protein | Mean EC$_{50}$ ± SD (from ELISA)[a] (ng/mL) | Mean EC$_{50}$ ± SD (from Bradford)[a] (ng/mL) |
| --- | --- | --- |
| Wild type IL-11 (R&D Systems) | 4.0 ± 1.1 | Not determined |
| Wild type IL-11 (Bolder BioTechnology) | 4.9 ± 0.8 | 14.7 ± 2.3 |
| P24C | 4.8, 5.6 | 17, 20 |
| 20 kDa-PEG-P24C | 2.0 | 21 |

TABLE 2-continued

In vitro bioactivities of insect cell-expressed IL-11, IL-11 cysteine muteins and PEGylated IL-11 cysteine muteins.

| IL-11 protein | Mean EC$_{50}$ ± SD (from ELISA)[a] (ng/mL) | Mean EC$_{50}$ ± SD (from Bradford)[a] (ng/mL) |
| --- | --- | --- |
| A162C | 6.6 ± 1.7 | 13.8 ± 3.5 |
| 20 kDA-PEG-A162C | 3.0 ± 0.6 | 18.6 ± 3.8 |
| *200C | 5.3 ± 1.7 | 8.7 ± 2.7 |
| 20 kDA-PEG-*200C | 1.1 ± 0.3 | 8.7 ± 2.2 |

[a] Mean ± standard deviation (SD) for at least 3 assays for each protein. Individual assay results are shown when there were less than 3 assays performed for a particular protein.

For larger scale preparation of PEG-*200C for animal studies, baculovirus supernatants were clarified by centrifugation. The pH of the clarified supernatant was then adjusted to pH 7.0, centrifuged again and filtered through a 0.45 micron filter. The IL-11*200C protein was purified in a single step procedure using Anti-FLAG M2 Affinity Gel (Sigma). The affinity gel was washed with three column volumes of 0.1M glycine pH 3.0, 0.02% Tween 20, 10% glycerol, then equilibrated with 5 column volumes of 50 mM Tris pH 7.5, 150 mM NaCl, 0.02% Tween 20 and 10% glycerol. The washed resin was added to the clarified supernatant and batch loaded at 4° C. overnight on a roller bottle apparatus. The resin was collected in a Pharmacia XK column and the resin washed with the Tris buffer until the A$_{280}$ reached baseline. The bound protein was eluted with 0.1 M glycine pH 3.0 and fractions collected and neutralized with 1.0 M Tris pH 9.2. Column fractions were analyzed by SDS-PAGE and the fractions containing the IL-11*200C protein were pooled.

Larger scale PEGylation reactions included 1-2 mg of the IL-11 *200C protein, a 20× molar excess of 20 kDa maleimide PEG and a 20× molar excess of TCEP. Reactions were performed at pH 8.0 at room temperature. After 2 hours, the PEGylation reaction mixture was diluted 10-fold with 20 mM NaPO$_4$ pH 6.0-7.0, 0.02% Tween 20, 10% glycerol (Buffer A) and loaded onto a 1 ml Hi Trap S-Sepharose column equilibrated in Buffer A. The column was washed with equilibration buffer and the bound proteins eluted with a 20 mM NaPO$_4$ pH 6.0-7.0, 0.02% Tween 20, 10% glycerol, 500 mM NaCl (Buffer B) step. This step served to concentrate the material prior to separation of the PEGylated and unmodified forms of the protein via size exclusion chromatography. A Superdex 200 10/30 column was equilibrated with 50 mM NaPO$_4$ pH 7.0, 150 mM NaCl, 10% glycerol. After equilibration a 0.5 ml sample was loaded onto the sizing column and an isocratic gradient was run. Column fractions were analyzed by SDS-PAGE and the fractions containing the PEGylated IL-11*200C were pooled. Similar procedures were used to prepare the IL-11 *200C protein modified with a branched 40 kDa-maleimide PEG.

Example 5

Pharmacokinetics and Efficacy in Normal Rats

The inventors performed pharmacokinetic (PK) studies of the PEG-IL-11 *200C proteins to compare their circulating half-lives to that of a recombinant human IL-11 product (Neumega®, American Home Products) in rats. Male Sprague-Dawley rats weighed 335-386 g at the beginning of the study. Both intravenous and subcutaneous pharmacokinetic data were obtained. 20 kDa-PEG-IL-11 (*200C) and 40 kDa-PEG-II-11(*200C) were prepared according to Example 4. For the intravenous delivery studies, rats received an intravenous bolus injection (0.1 mg/kg) of 20 kDa-PEG-IL-11 (*200C), 40 kDa-PEG-IL-11 (*200C) or Neumega. Three rats were used for each protein tested. Blood samples were drawn prior (time 0) to injection of the test compounds and at 0.083, 0.5, 1, 2, 4, 10, 24, 48, 72, 120, 168, 216 and 264 h post-injection. Subcutaneous delivery studies were performed in a similar manner but the test compounds were administered subcutaneously and blood samples were drawn at 0.5, 1, 2, 4, 10, 24, 48, 72, 120, 168, 216 and 264 h post-injection. Plasma levels of the proteins were measured using human IL-11 ELISA kits (R & D Systems, Minneapolis, Minn.). Standard curves were determined for each protein to measure the relative sensitivity of the ELISA for detecting the proteins.

The effect of the proteins on levels of circulating platelets in the rats also was determined. Complete blood cell (CBC) analyses were performed on blood samples taken at 0, 72, 120, 168, 216 and 264 h post injection. CBC analyses were performed on a Hemavet HV950FS Multispecies Hematology Analyzer. These studies demonstrated that plasma half-lives of the 20 kDa-PEG-IL-11 (*200C) and the 40 kDa-PEG-IL-11 (*200C) proteins were substantially greater than the half-life of Neumega. Tables 3 and 4 show plasma levels of these proteins as a function of time following intravenous and subcutaneous injection, respectively. Following intravenous injection, Neumega is cleared rapidly from the circulation and cannot be detected at 10 hours post injection. In contrast, the PEGylated IL-11 cysteine analogs are easily detected and are present at 2 to 3 orders of magnitude higher concentration than Neumega at 10 h post-injection. The 20 kDa-PEG-IL-11 (*200C) protein is still detectable 24 h post injection, but is below the detection level at 48 h post-injection. The 40 kDa-PEG-IL-11 (*200C) protein is still detectable up to 48 h post injection, but was below the assay detection limit at 72 h post-injection. The subcutaneous PK study gave similar results. The Neumega was undetectable at 10 h post injection and was cleared much more rapidly than the PEGylated IL-11 (*200C) proteins, which were both detectable 24 h post-injection, but were below detection levels at 48 h post-injection.

TABLE 4

Plasma levels (expressed in pg/mL) of IL-11 (Neumega), 20 kDa-PEG-IL11 (*200C), or 40 kDa-PEG-IL11 (*200C), following a single subcutaneous injection of 100 µg protein/kg of in Sprague-Dawley rats.

| Time post-injection (h) | IL-11 (Neumega) | 20 kDa-PEG-IL11 (*200C) | 40 kDa-PEG-IL11 (*200C) |
|---|---|---|---|
| 0 | 0 | 0 | 0 |
| 0.5 | 10,223 ± 1,621 | 0 | 0 |
| 1 | 9,765 ± 1,453 | 0 | 0 |
| 2 | 5,962 ± 2,438 | 541 ± 946 | 5,002 ± 4,327 |
| 4 | 3,375 ± 699 | 2,257 ± 447 | 42,757 ± 38,747 |
| 10 | 0 | 18,959 ± 18,283 | 49,387 ± 31,482 |
| 24 | 0 | 1,248 ± 1,082 | 13,617 ± 11,354 |
| 48 | 0 | 0 | 0 |

Data are means ± SEM.

The inventors discovered that the PEGylated IL-11 (*200C) proteins are potent stimulators of platelet production in rats. Table 5 shows the levels of circulating platelets over time in rats (N=3/group) that received 20 kDa-PEG-IL-11 (*200C), 40 kDa-PEG-IL-11 (*200C), or Neumega (IL-11) by intravenous administration in the PK study described above. A single injection of Neumega did not have an effect on circulating platelet levels in these rats. In contrast a single injection of 20 kDa-PEG-IL-11 (*200C) or 40 kDa-PEG-IL-11 (*200C) caused an increase in circulating platelet levels that is apparent at 72 hours post-injection and peaks at 120 hours post-injection. For the 20 kDa-PEG-IL-11 (*200C) protein the peak value is about 30% over baseline at 72 h and returns to baseline by 216 h. Injection of the 40 kDa-PEG-IL-11 (*200C) caused a greater increase in platelets, about 60% over baseline at 72 hours and the platelet levels remain elevated until 264 hours post-injection. Similar results were seen with subcutaneous injection of the compounds (Table 6). These results demonstrate the superior potency of 20 kDa-PEG-IL-11 (*200C) and 40 kDa-PEG-IL-11 (*200C), as compared to Neumega, at stimulating increases in levels of circulating platelets. These results demonstrate that a single injection of a PEGylated IL-11 protein is capable of stimulating increases in circulating platelets whereas a single injection of IL-11 (Neumega) has no effect on circulating platelet levels.

TABLE 3

Plasma levels (expressed in pg/mL) of IL-11 (Neumega), 20 kDa-PEG-IL11 (*200C), or 40 kDa-PEG-IL11 (*200C), following a single intravenous injection of 100 µg protein/kg in Sprague-Dawley rats.

| Time post-injection (h) | IL-11 (Neumega) | 20 kDa-PEG-IL11 (*200C) | 40 kDa-PEG-IL11 (*200C) |
|---|---|---|---|
| 0 | 0 | 0 | 0 |
| 0.083 | 308,708 ± 27,386 | 2,457,267 ± 160,389 | 2,135,873 ± 292,238 |
| 0.5 | 58,735 ± 18,337 | 1,671,186 ± 89,915 | 1,478,560 ± 268,546 |
| 1 | 5,040 ± 1,567 | 1,256,469 ± 78,250 | 1,234,776 ± 124,842 |
| 2 | 500 ± 347 | 869,329 ± 90,768 | 1,091,975 ± 188,987 |
| 4 | 90 ± 17 | 566,519 ± 28,022 | 953,435 ± 146,025 |
| 10 | 0 | 177,223 ± 2,942 | 595,235 ± 135,782 |
| 24 | 0 | 1,120 ± 971 | 115,064 ± 53,529 |
| 48 | 0 | 0 | 3,932 ± 3,488 |

Data are means ± SEM.

TABLE 5

Circulating platelet counts (expressed in thousands/μL) in animals receiving a single intravenous injection of 100 μg protein/kg of Neumega (IL-11), 20 kDa-PEG-IL11 (* 200C), or 40 kDa-PEG-IL11 (* 200C).

| Hours post-injection (h) | Neumega (IL-11) | 20 kDa-PEG IL-11 (* 200C) | 40 kDa-PEG IL-11 (* 200C) |
|---|---|---|---|
| 0 | 770 ± 111 | 748 ± 40 | 743 ± 58 |
| 72 | 748 ± 74 | 868 ± 52 | 956 ± 52 |
| 120 | 711 ± 4 | 1048 ± 30 * | 1294 ± 103 * |
| 168 | 728 ± 38 | 924 ± 30 * | 1146 ± 121 * |
| 216 | 690 ± 41 | 770 ± 17 | 962 ± 69 * |
| 264 | 667 ± 21 | 738 ± 36 | 808 ± 63 |

Data are means ± SEM.
p < 0.05 versus Neumega at same time post-injection using a Student's two-tailed t-test.

TABLE 6

Circulating platelet counts (expressed in thousands/μL) in animals receiving a single subcutaneous injection of 100 μg protein/kg of Neumega, 20 kDa-PEG-IL11 (* 200C), or 40 kDa-PEG-IL11 (* 200C).

| Hours post-injection (h) | Neumega | 20 kDa-PEG IL11 (* 200C) | 40 kDa-PEG IL11 (* 200C) |
|---|---|---|---|
| 0 | 719 ± 30 | 848 ± 120 | 711 ± 78 |
| 24 | 747 ± 41 | 805 ± 93 | 720 ± 74 |
| 72 | 869 ± 31 | 1110 ± 124 | 848 ± 52 |
| 120 | 885 ± 14 | 1197 ± 41 * | 1166 ± 59 * |
| 168 | 804 ± 54 | 1116 ± 89 * | 1128 ± 82 * |
| 216 | 794 ± 20 | 971 ± 82 | 887 ± 71 |
| 264 | 718 ± 29 | 856 ± 79 | 803 ± 93 |

Data are means ± SEM.
p < 0.05 versus Neumega at same time post-injection using a Student's two-tailed t-test.

Example 6

Efficacy of PEG-IL-11 (*200C) in Myelosuppressed Rats

The inventors found that the PEGylated IL-11 (*200C) cysteine mutein accelerates recovery from thrombocytopenia in cyclophosphamide-treated rats following every-other-day subcutaneous dosing. Male Sprague-Dawley rats were obtained from Harlan Sprague-Dawley. The rats weighed approximately 200 g at study initiation. Animals were acclimated for 8 days prior to being placed on the study. On day −1, blood samples were drawn and CBC analyses performed. Based on these results, rats were randomized to groups of 5 according to their platelet levels. One group of rats received subcutaneous injections of vehicle solution (Delbucco's phosphate buffered saline) on days 1, 3, 5 and 7. A second group of rats received an intraperitoneal injection of 100 mg/kg of cyclophosphamide (CPA) on day 0 and subcutaneous injections of vehicle solution on days 1, 3, 5 and 7. A third group of rats received an intraperitoneal injection of 100 mg/kg of CPA on day 0 and subcutaneous injections of 100 μg protein/kg of 20 kDa-PEG-IL-11 (*200C) on days 1, 3, 5 and 7. A fourth group of rats received an intraperitoneal injection of 100 mg/kg of CPA on day 0 and subcutaneous injections of 100 μg protein/kg of 40 kDa-PEG-IL-11 (*200C) on days 1, 3, 5 and 7. Blood samples for CBC analysis were obtained on days −1, 1, 3, 5, 6, 7, 8, 9, 10 & 13. Blood samples of approximately 50-100 μL were collected into EDTA Microvette tubes (Sarstedt) and analyzed with a Hemavet 950FS (Drew Scientific) to determine levels of circulating platelets. The data are presented in Table 7. In animals that did not receive CPA, but did receive injections of vehicle, platelet levels did not change significantly over the course of the experiment. In contrast, in animals that received CPA followed by injections of vehicle, platelet levels decreased from an average of $1,166 \times 10^3$ cells/μL on day −1 to an average of $644 \times 10^3$ cells/μL on day 5. In animals that received 20 kDa-PEGylated IL-11 (*200C), the platelet levels decreased less to an average of $909 \times 10^3$ cells/μL and this nadir occurred on day 3. By day 5 platelet levels were already increasing in the animals in this group and by day 6 platelet levels in these animals had returned to baseline levels. In contrast, platelet levels did not return to baseline levels in the CPA+ vehicle control group until day 7. Similar results were seen in rats receiving 40 kDa-PEGylated IL-11 (*200C). In animals that received 40 kDa-PEGylated IL-11 (*200C), the platelet levels decreased less to an average of $837 \times 10^3$ cells/μL and this nadir occurred on day 3. By day 5 platelet levels were already increasing in the animals in this group and by day 6 platelet levels in these animals had returned to baseline levels. These results demonstrate the ability of the PEGylated IL-11 (*200C) protein to reduce the severity of thrombocytopenia and to accelerate the recovery to normal platelet levels in myelosuppressed animals The compound could also similarly be used to reduce the severity of thrombocytopenia and to accelerate the recovery to normal platelet levels in animals or humans rendered thrombocytopenic as result of other chemical treatments, radiological treatments, disease, or idiopathic causes. Similar experiments can be performed using different dosing regimens such as every day, every third day and a single injection of the PEG-IL-11 proteins.

TABLE 7

Circulating platelet counts (expressed in thousands/μL) in animals receiving every other day subcutaneous injections of vehicle solution or 100 μg protein/kg of 20 kDa-PEG-IL11 (* 200C) or 40 kDa-PEG-IL11 (* 200C).

| Days post-injection | Vehicle (no CPA) | CPA + Vehicle | CPA + 20 kDa-PEG-IL11 (* 200C) | CPA + 40 kDa-PEG-IL11 (* 200C) |
|---|---|---|---|---|
| −1 | 1161 ± 38 | 1166 ± 40 | 1167 ± 30 | 1168 ± 53 |
| 1 | 1197 ± 42 | 1197 ± 41 | 1172 ± 47 | 1183 ± 13 |
| 3 | 1198 ± 41 | 847 ± 58 | 909 ± 34 | 837 ± 17 |
| 5 | 1180 ± 46 | 644 ± 74 | 919 ± 91 * | 947 ± 67 * |
| 6 | 1197 ± 80 | 885 ± 59 | 1257 ± 29 * | 1336 ± 106 * |
| 7 | 1226 ± 48 | 1201 ± 41 | 1642 ± 44 * | 1721 ± 36 * |
| 8 | 1183 ± 20 | 1637 ± 21 | 1940 ± 58 * | 2109 ± 19 * |
| 9 | 1150 ± 119 | 1834 ± 25 | 2346 ± 69 * | 2263 ± 104 * |
| 10 | 1205 ± 54 | 1714 ± 45 | 2404 ± 129 * | 2624 ± 54 * |
| 13 | 1069 ± 44 | 1324 ± 48 | 1679 ± 38 * | 1670 ± 39 * |

Control animals did not receive CPA but did receive every other day subcutaneous injections of vehicle solution. Data are means ± SEM.
* p < 0.05 versus CPA-treated rats receiving vehicle at same time post-injection using a Student's two-tailed t-test.

Example 7

Construction of a Synthetic IL-11 Gene for *E. coli* Expression

The IL-11 coding sequence contains a large number of codons that do not occur frequently in *E. coli* proteins that are expressed at high levels. The presence of significant numbers of these so-called "rare codons" in the coding sequences of heterologous proteins expressed in *E. coli* can dramatically reduce expression levels. Therefore we constructed a "synthetic" IL-11 gene by oligonucleotide assembly in which only E. coli—preferred codons were employed. To facilitate cloning the gene was constructed with a Mlu I recognition site at its 5' end and an Eco RI recognition site at its 3' end. The synthetic IL-11 gene was digested with Mlu I-Eco RI and ligated into a derivative of plasmid pUC18 that was digested with Mlu I and Eco RI and treated with calf intestinal phosphatase. The resulting plasmid was termed pBBT375. We constructed the IL-11 synthetic sequence so that the initial proline residue (P22) of the mature protein was deleted. The sequence of this synthetic IL-11 del P22 gene is given in SEQ ID NO:51. SEQ ID NO:51 encodes a synthetic IL-11 amino acid sequence represented herein by SEQ ID NO:52. This synthetic gene was used to express IL-11 and IL-11 cysteine muteins in the *E. coli* cytoplasm and in the intein fusion protein system (New England BioLabs, Beverly, Mass.) described in Examples 8 and 9.

Example 8

Cytoplasmic Expression of IL-11 and IL-11 Cysteine Muteins in *E. coli*

IL-11 del P22 was expressed in the *E. coli* cytoplasm by inserting the synthetic IL-11 gene into expression vector pET21a+ (Novagen). This vector utilizes the phage T7 promoter and requires that the plasmid be inserted into an *E. coli* strain containing the T7 RNA polymerase, such as BL21 (DE3) (Novagen). A translational coupler sequence was created using synthetic oligonucleotides and was incorporated at the 5' end of the gene to facilitate initiation of translation. In addition, DNA encoding an initiator methionine residue was added to DNA encoding the N-terminus of the mature IL-11 del P22 protein. Similar procedures could be used to express IL-11 containing P22.

In addition to the del P22 construct, we made an IL-11 mutant that deleted amino acid residues 22 through 26 (deletes PGPPP; referred to as IL-11 del 22-26). We also made an IL-11 mutant that deleted amino acid residues 22 through 29 (deletes PGPPPGPP; referred to as IL-11 del 22-29). Each deletion mutant was made by PCR using mutagenic oligonucleotides (Scharf, 1990).

After confirming that the DNA sequences were correct, the three N-terminal deletion mutants were incorporated into the structural gene for IL-11 using standard recombinant DNA methods. The IL-11 genes were then subcloned into vector pET21a+. The plasmids were transformed into *E. coli* strain BL21 (DE3), and expression of the IL-11 deletion variants were induced with IPTG. We found that expression of IL-11 del P22 was undetectable when a total *E. coli* cell lysate of this strain was analyzed by SDS-PAGE and stained with Coomassie Blue. However, both IL-11 del 22-26 and IL-11 del 22-29 did express well as judged by SDS-PAGE of total *E. coli* cell lysates.

The inventors hypothesized that the string of 3 prolines near the N-terminus (P24, P25, and P26) was inhibiting translation. This theory was tested by constructing additional N-terminal mutants that deleted amino acids 22-23 (referred to as IL-11 del 22-23), or deleted amino acids 22-24 (referred to as IL-11 del 22-24), or deleted amino acids 22-25 (referred to as IL11 del 22-25). The mutant genes were constructed by site directed mutagenesis and cloned into pET21a+. The resulting plasmids were transformed into BL21 (DE3) for expression studies. Based on SDS-PAGE analysis of total cell lysates, the inventors found that expression of IL-11 del 22-23 was undetectable, IL-11 del 22-24 was expressed at a moderate level, and IL-11 del 22-25 expressed well. These data indicate that deleting amino acids 22-24 or 22-25 improves expression of IL-11 proteins in *E. coli*.

The inventors also constructed three cysteine substitution mutants in the IL11 del P22 gene. These mutants were IL-11 P24C/del P22, IL-11 P25C/del P22, and IL-11 P26C/del P22. The IL-11 P24C/del P22 expressed well, whereas IL-11 P25C/del P22 and IL-11 P26C/del P22 exhibited moderate expression. The data indicate that deleting any or all of P24, P25 or P26, or substituting non-proline amino acids for these proline residues improves expression of IL-11 proteins in *E. coli*, and potentially in other host cells and organisms. Non-proline amino acids that may be substituted for P24, P25 and P26 include alanine, cysteine, serine, threonine, glycine, asparagine, glutamine, aspartic acid, glutamic acid, leucine, isoleucine, valine, phenylalanine, tryptophan, histidine, lysine, methionine, arginine and tyrosine. Other non-natural amino acids known in the art also may be substituted for P24, P25 or P26. Cysteine is a preferred amino acid that can be substituted for P24, P25 or P26. The inventors also constructed an IL-11 mutant that combines the del 22-29 and *200C mutations (IL-11 del 22-29 *200C).

For expression and purification of the IL-11 proteins, cultures were grown at 37° C., induced with 0.5 mM IPTG and grown for an additional 3 h. Cells were pelleted by centrifugation and stored at −20° C. until further processing. Cells from a total of 1.2 L were resuspended in 10 mM Tris, 1 mM EDTA, 0.1% Tween-20, 1 mM TCEP at pH 7.5 and mechanically lysed by one pass through a NIRO homogenizer at 600 bar. The cell lysate was centrifuged at 8000 rpm for 30 minutes, using a Beckman JLA 10.5 rotor. The supernatant was collected and the pellet stored at −20° C. The supernatant containing soluble IL-11 proteins was loaded onto a 5 ml S Sepharose HP column that was pre-equilibrated in S buffer A (20 mM Tris, 10% glycerol, 0.05% Tween-20, 1 mM TCEP, pH 6.0). IL-11 proteins were eluted using a 0 to 60% gradient of S buffer B (20 mM Tris, 10% glycerol, 0.05% Tween-20, 1 mM TCEP, 1M NaCl, pH 6.0) over 20 column volumes. The IL-11 proteins began eluting at 120 mM NaCl. Fractions were analyzed using SDS-PAGE. Fractions containing the IL-11 proteins were pooled and NaCl added to a concentration of 4M. The IL-11 protein was loaded onto a 2 ml Toyo Pearl Phenyl Sepharose column that was pre-equilibrated in phenyl buffer A (20 mM Tris, 4M NaCl, 10% glycerol, 0.05% Tween-20, pH 9.0) at room temperature. The IL-11 protein was eluted using phenyl buffer B (20 mM Tris, 10% glycerol, 0.05% Tween-20, pH 9.0) and elutes at approximately 70% buffer B (300 mM NaCl). Fractions were analyzed using SDS-PAGE. Fractions containing IL-11 proteins are pooled, diluted 10-fold with S buffer A and loaded onto a pre-equilibrated 1 ml CM Sepharose column. Proteins were eluted using S buffer B in which the proteins elute at about 200 mM NaCl. Fractions were analyzed using SDS-PAGE and fractions containing IL-11 proteins were pooled and quantified by Bradford Assay. The IL-11 del P22/P25C protein prepared this way was PEGylated as follows. PEGylation was achieved by three additions of 2-fold molar excess 20K PEG-maleimide (6-fold molar excess total) and 5-fold (15-fold total) molar excess TCEP, over a 2 hour period (every 40 minutes) at pH 7.5, room temperature. 80 to 90% of the IL-11 mutein was converted to the monoPEGylated form. The inventors found that multiple additions of TCEP and PEG reagent to the cysteine analogs often gave higher yields of PEGylated protein than a single addition of TCEP and PEG reagent. The PEGylation reaction was diluted 4× with PEG buffer A (20 mM Tris, 10% glycerol, 0.05% Tween-20, pH 6.0) and loaded onto a pre-equilibrated 1 ml S Sepharose column and eluted using a 0 to 100% gradient of PEG buffer B (20 mM Tris, 10% glycerol, 0.05% Tween-20, pH 6.0, 1M NaCl). This column step separates PEGylated protein from non-PEGylated protein. Other reducing agents including, but not limited to, dithiothreitol, BME, cysteamine, reduced glutathionine and cysteine, can be substituted for TCEP in the procedures described above. The PEGylation reaction also may be performed by exposing the IL-11 mutein to the reducing agent and then dialyzing the reducing agent away prior to exposure of the reduced protein to the PEG reagent.

Insoluble IL-11 proteins present in the NIRO cell pellets were solubilized in 2 mls of 20 mM Tris, 8M urea, 50 mM cysteine, pH 7.5 and gently rocked at room temperature for 2 hours. The solution was then diluted 10× into refolding buffer containing 20 mM Tris, 0.1% Tween-20, pH 7.5 and incubated overnight at 4° C. The refold was diluted 5× with S buffer A and the pH was adjusted to 6.0 and loaded onto a 1 ml S Sepharose column and purified as described above. The IL-11 proteins eluting from the S column were further purified using the Phenyl Sepharose column followed by the CM column. The purified IL-11 proteins were quantified by Bradford analysis. The IL-11 proteins prepared in this manner can be PEGylated and purified as described above.

The purified cysteine muteins and the purified PEGylated del P22/P25C cysteine mutein were assayed for biological activity vs. a wild type IL-11 control in the B9-11 in vitro cell-line proliferation assay. All of the purified cysteine muteins and the purified PEGylated cysteine muteins were biologically active, as measured by their ability to stimulate proliferation of B9-11 cells (Table 8). The $EC_{50}$s of the purified cysteine muteins were within 4-fold of the $EC_{50}$s of the wild type IL-11 control proteins. The $EC_{50}$ of the purified PEGylated del P22/P25C cysteine muteins was within 3-fold of the $EC_{50}$ of the wild type IL-11 control proteins.

TABLE 8

In vitro bioactivities of IL-11 cysteine muteins and PEGylated cysteine muteins in the B9-11 cell proliferation assay.

| IL-11 protein | Mean $EC_{50}$ ± SD (from Bradford) [a] (ng/mL) |
|---|---|
| Wild type IL-11 (Neumega) | 3.2 ± 0.94 |
| IL-11 del 22-29 | 5.4 ± 0.46 |
| IL-11 del 22-26 | 2.4 ± 0.75 |
| IL-11 del 22-29 *200C | 12.5 ± 0.71 |
| IL-11 del P22/P25C | 3.9 ± 0.97 |
| 20 kDA-PEG del P22/P25C | 7.1 ± 2.5 |
| IL-11 del P22/P24C | 4.8 ± 0.28 |

[a] Mean ± SD for at least 3 assays for each protein. All proteins were purified from the soluble fraction of the Niro cell lysates except the IL-11 del 22-29 *200C protein, which was purified from the Niro cell pellet.

Example 9

Expression of IL-11 and IL-11 Cysteine Muteins in *E. coli* using the Intein system The expression vector pTYB11 (New England Biolabs) contains a chitin binding domain (CBD) flanked by a yeast intein sequence. The multiple cloning site is positioned to allow one to fuse a protein of interest to the intein. After expression, the fusion product is bound to a chitin affinity column, and the protein of interest is cleaved from the fusion protein and eluted by incubating the column in a reducing agent such as dithiothreitol (DTT). Other reducing agents including, but not limited to, BME, TCEP, cysteamine, reduced glutathionine and cysteine, can be substituted for DTT. The protein of interest can be recovered without any non-native residues attached to its N-terminus.

The synthetic IL-11 del P22 gene was cloned into pTYB11 as follows. A SacI-EcoRI fragment encoding residues 38 to 199 and the termination codon of IL-11 del P22 was cloned from pBBT375 into pUC19 cut with Sac I and Eco RI, producing the plasmid pBBT760.

The 5' region of the synthetic IL-11 gene was PCR-amplified from pBBT375 using primers BB915 (5' TGCTCTA-GAGCTCTTCCAACGGTCCGCCGCCGGGT; SEQ ID NO:49) and BB900 (5' CCTAGGGAGCTCAGCACGCGG; SEQ ID NO:50). The resulting PCR fragment was digested with Xba I and Sac I, and cloned into pBBT760 digested with the same restriction enzymes and phosphatase-treated, yielding plasmid pBBT782. After confirming the sequence of the PCR-generated region of the IL-11 gene, pBBT782 was digested with Sap I and Eco RI. The released ~550 bp fragment was gel purified and inserted into pTYB11 that had been similarly digested. The resulting plasmid, pBBT785, was transformed into the *E. coli* strain ER2566 (New England BioLabs), and the derived strain, BOB991 was induced with IPTG to express the CBD-Intein-IL-11 fusion. After a 5 hr induction at 25° C., cells were collected by centrifugation, and a portion of the cell pellet was analyzed by SDS-PAGE. A protein with a mobility expected for a CBD-Intein-IL-11 fusion (76.4 kDa) was observed in total cell lysate of BOB991 that was not seen in the isogenic strain lacking the IL-11 gene. Further, Western blot analysis of the BOB991 lysate showed that the putative CBD-Intein-IL-11 fusion reacted with a commercial anti-IL-11 antibody (R&D Systems).

The remaining cells were mechanically disrupted, and the soluble portion of the lysate was passed through a chitin affinity column, which specifically bound the CBD-Intein-IL-11 fusion. After washing with column buffer (20 mM Tris, pH 8.0, 0.5M NaCl, 1 mM EDTA, 0.1% Tween-20), the chitin column was then flushed with 3 column volumes of the column buffer containing 50 mM DTT. The flow to the column was then stopped, and the column was left overnight at room temperature. During this overnight incubation, the bond fusing IL-11 to the intein is cleaved. IL-11 was then eluted from the column with 5 column volumes of column buffer. Column fractions were analyzed by non-reducing SDS-PAGE and the fractions containing IL-11 were pooled. The cleaved IL-11 had an apparent molecular weight of approximately 24 kDa by non-reducing SDS-PAGE. In some cases the IL-11 protein was further purified using an S-Sepharose column. The chitin pool was diluted 1:10 with buffer A (20 mM MES, pH 6.0, 10% glycerol, 0.1% Tween-20) and loaded onto a 1 ml S-Sepharose HiTrap column (GE Healthcare) equilibrated in Buffer A. The bound proteins were eluted with a linear salt gradient from 0-50% Buffer B (Buffer A containing 1M NaCl). Column fractions were analyzed by non-reducing SDS-PAGE and the fractions containing IL-11 were pooled. Protein concentrations were determined using a Bradford assay (Bio-Rad Laboratory). In some cases it may be preferable to pass the pooled IL-11 proteins isolated from the chitin column through a Q-sepharose column to remove *E. coli* endotoxin prior to the S-Sepharose column step. Conditions can be chosen such that IL-11 does not bind the Q-Sepharose column and elutes in the flow-though, whereas endotoxin does bind the Q-Sepharose column.

Similar procedures were used to express the following IL-11 del P22 cysteine muteins: P24C, P25C, D69C, L72C, E123C and *200C. Similar procedures can be used to express and purify other IL-11 cysteine muteins, and IL-11 variants containing amino acid substitutions, amino acid deletions, amino acid additions, amino acid insertions, and IL-11 fusion proteins.

Example 10

PEGylation of the *E. coli*-Expressed IL-11 Cysteine Muteins

Aliquots of 200 to 300 μg of the purified IL-11 cysteine muteins prepared as described in Example 9 were incubated with a 10-fold molar excess of TCEP and a 10-fold molar excess of 20 kDa-maleimide-PEG (Nektar, Inc., Huntsville, Ala.). Approximately 3.3-fold molar excess of 20 kDa-maleimide was added to the reaction three times for every 40 minutes (at 0, 40, 80 min). After a total of 2 h incubation at room temperature, the PEGylation mixture was diluted 10× with Buffer A (20 mM MES, pH 6.0, 10% glycerol, 0.1% Tween-20). This pool was loaded onto a 1 ml S-Sepharose HiTrap column (GE Healthcare) equilibrated in Buffer A. The bound proteins were eluted with a linear salt gradient from 0-50% Buffer B (Buffer A containing 1M NaCl). Column fractions were analyzed by non-reducing SDS-PAGE. The PEGylated IL-11 cysteine muteins eluted at approximately 100-200 mM NaCl. Fractions containing purified 20 kDa PEG-IL-11 cysteine mutein protein were pooled. The IL-11 cysteine muteins modified with a 10 kDa PEG-maleimide and a 40 kDa PEG-maleimide were prepared using this same protocol.

The IL-11 del P22/*200C protein also was PEGylated using the following procedure. Aliquots of 1 mg of the purified IL-11 *200C mutein prepared as described in Example 9 were incubated with a 20-fold molar excess of TCEP (Pierce Chemical Company) and a 20-fold molar excess of 20 kDa-maleimide-PEG (Nippon Oil and Fat, NOF). After a 2 h incubation at room temperature, the PEGylation mixture was diluted 10× with Buffer A (20 mM MES, pH 6.0, 10% glycerol, 0.1% tween-20) and loaded onto a 1 ml S-Sepharose HiTrap column (GE Healthcare) equilibrated in Buffer A. The bound proteins were eluted with a linear salt gradient from 0-25% Buffer B (Buffer A containing 1M NaCl). Column fractions were analyzed by non-reducing SDS-PAGE. The mono-PEGylated IL-11 del P22 *200C protein eluted at approximately 140 mM NaCl. Fractions containing purified mono-PEGylated IL-11 del P22 *200C protein were pooled. The IL-11 del P22 *200C protein modified with a 30 kDa PEG-maleimide (NOF) and a 40 kDa branched PEG-maleimide (Nektar, Inc.) were prepared using this same protocol. Similar procedures can be used to prepare PEGylated derivatives of other IL-11 cysteine muteins.

The purified IL-11 cysteine muteins and the purified PEGylated cysteine muteins were assayed for biological activity vs. a wild type IL-11 control in the B9-11 in vitro cell-line proliferation assay. All of the purified cysteine muteins and the purified PEGylated cysteine muteins were biologically active, as measured by their ability to stimulate proliferation of B9-11 cells. The $EC_{50}$s of the purified cysteine muteins ranged from indistinguishable from the $EC_{50}$ of the wild type IL-11 control to approximately 4.5-fold higher than the $EC_{50}$ of the wild type control. The $EC_{50}$s of the purified PEGylated cysteine muteins ranged from approximately 3-fold to 6-fold higher than wild type IL-11.

TABLE 9

In vitro bioactivities of intein-expressed IL-11 cysteine muteins and PEGylated IL-11 cysteine muteins in the B9-11 cell proliferation assay.

| IL-11 protein | Mean $EC_{50}$ ± SD (ng/mL) |
|---|---|
| Wild type IL-11 (Neumega) | 3.2 ± 0.94 |
| IL-11 del P22 | 3.3 ± 0.64 |
| P24C/del P22 | 12.0 ± 3.5 |
| 20 kDa-PEG P24C/del P22 | 11.3 ± 6.4 |
| P25C/del P22 | 2.3 ± 0.10 |
| 20 kDA-PEG P25C/del P22 | 16 ± 4.0 |
| D69C/del P22 | 7.7 ± 0.14 |
| L72C/del P22 | 13.5 ± 2.1 |
| E123C/del P22 | 6.9 ± 0.21 |
| *200C/del P22 | 3.8 ± 1.3 |
| 20 kDa-PEG-*200C/del P22 | 9.1 ± 2.6 |
| 30 kDa-PEG-*200C/del P22 | 9.9 ± 1.9 |
| 40 kDa-PEG-*200C/del P22 | 24 ± 5.6 |

Protein concentrations were determined from Bradford analysis.

Example 11

Efficacy of PEGylated *E. coli*-Expressed IL-11 Cysteine Muteins in Normal Rats

The inventors determined whether a single subcutaneous injection of IL-11 *200C/del P22 modified with 20 kDa-, 30 kDa- and 40 kDa-PEGs, and prepared as described in Example 10, stimulated production of platelets in rats. Experiments were performed as described in Example 5. Rats received a single bolus injection of the PEG-IL-11 proteins, Neumega (IL-11) or placebo (PBS). Three rats were used for each protein tested. CBC analyses were performed on blood samples taken on day 0, 1, 3, 5, 7, 9 and 11 post injection. CBCs were performed on a Hemavet HV950FS Multispecies Hematology Analyzer.

As shown in Table 10, a single injection of placebo or Neumega did not have an effect on circulating platelet levels in these rats. In contrast, a single injection of 20 kDa-PEG-IL-11 (*200C/del P22), 30 kDa-PEG-IL-11 (*200C/del P22) or 40 kDa-PEG-IL-11 (*200C/del P22) caused an increase in circulating platelet levels that is apparent at 3 days post-injection and peaks at 5-7 days post-injection. These results demonstrate the superior potency of 20 kDa-PEG-IL-11 (*200C/del P22), 30 kDa-PEG-IL-11 (*200C/del P22) and 40 kDa-PEG-IL-11 (*200C/del P22), as compared to Neumega, at stimulating increases in levels of circulating platelets. These results demonstrate that a single injection of a PEGylated IL-11 protein is capable of stimulating increases in circulating platelets whereas a single injection of unPEGylated IL-11 (Neumega) has no effect on circulating platelet levels.

TABLE 10

Circulating platelet counts (expressed in thousands/μL) in animals receiving a single subcutaneous injection of placebo (PBS) or 100 μg protein/kg of Neumega (IL-11), 20 kDa-PEG-IL11 (*200C/del P22), 30 kDa-PEG-IL11 (*200C/del P22), or 40 kDa-PEG-IL11 (*200C/del P22).

| Day | Placebo | Neumega (IL-11) | 20 kDa-PEG (*200C/del P22) | 30 kDa-PEG (*200C/del P22) | 40 kDa-PEG (*200C/del P22) |
|---|---|---|---|---|---|
| 0 | 1116 ± 61 | 1107 ± 41 | 1102 ± 78 | 1115 ± 42 | 1057 ± 28 |
| 1 | 1026 ± 25 | 915 ± 47 | 878 ± 21 | 887 ± 31 | 998 ± 23 |
| 3 | 976 ± 25 | 1058 ± 64 | 1166 ± 21 [a] | 1144 ± 46 [a] | 1160 ± 31 [a] |
| 5 | 1002 ± 36 | 968 ± 76 | 1425 ± 49 [a,b] | 1377 ± 96 [a,b] | 1320 ± 58 [a,b] |
| 7 | 1091 ± 35 | 1092 ± 47 | 1275 ± 74 | 1347 ± 87 [a] | 1410 ± 64 [a,b] |
| 9 | 1085 ± 49 | 1161 ± 32 | 1208 ± 54 | 1223 ± 61 | 1215 ± 49 |
| 11 | 1131 ± 45 | 1011 ± 55 | 1340 ± 92 [b] | 1156 ± 124 | 1245 ± 8 [b] |

Data are means ± SEM.
[a] $p < 0.05$ versus placebo at same time post-injection using a Student's two-tailed t-test.
[b] $p < 0.05$ versus Neumega at same time post-injection using a Student's two-tailed t-test.

Example 12

Efficacy of PEG-IL-11 (del 22/*200C) in Myelosuppressed Rats

We determined whether the PEGylated IL-11 (*200C/del P22) cysteine mutein prepared as described in Example 11, could accelerate recovery from thrombocytopenia in cyclophosphamide-treated rats following every-other-day subcutaneous dosing. Male Sprague-Dawley rats were obtained from Harlan Sprague-Dawley. The rats weighed approximately 220-240 g at study initiation. On day −1, blood samples were drawn and CBC analyses performed. Based on these results, rats were randomized to groups of 5 according to their platelet levels. One group of rats received subcutaneous injections of vehicle solution (phosphate buffered saline) on days 1, 3, 5 and 7. A second group of rats received an intraperitoneal injection of 100 mg/kg of cyclophosphamide (CPA) on day 0 and subcutaneous injections of vehicle solution on days 1, 3, 5 and 7. A third group of rats received an intraperitoneal injection of 100 mg/kg of CPA on day 0 and subcutaneous injections of 100 μg protein/kg of 20 kDa-PEG-IL-11 (*200C/del 22) on days 1, 3, 5 and 7. A fourth group of rats received an intraperitoneal injection of 100 mg/kg of CPA on day 0 and subcutaneous injections of 100 μg protein/kg of 30 kDa-PEG-IL-11 (*200C/del P22) on days 1, 3, 5 and 7. A fifth group of rats received an intraperitoneal injection of 100 mg/kg of CPA on day 0 and subcutaneous injections of 100 μg protein/kg of 40 kDa-PEG-IL-11 (*200C/del P22) on days 1, 3, 5 and 7. A sixth group of rats received an intraperitoneal injection of 100 mg/kg of CPA on day 0 and subcutaneous injections of 100 μg protein/kg of Neumega (IL-11) on days 1, 3, 5 and 7. Blood samples for CBC analysis were obtained on days −1, 1, 3, 5, 6, 7, 8, 9, 10 & 13. Certain of the day 3 blood samples were lost. Blood samples of approximately 50-100 μL were collected into EDTA Microvette tubes (Sarstedt) and analyzed with a Hemavet 950FS (Drew Scientific) to determine levels of circulating platelets. The data are presented in Table 11. In animals that did not receive CPA, but did receive injections of vehicle, platelet levels did not change significantly over the course of the experiment. In contrast, in animals that received CPA followed by injections of vehicle, platelet levels decreased from an average of $1,017 \times 10^3$ cells/μL on day −1 to an average of $306 \times 10^3$ cells/μL on day 5. In animals that received 20 kDa-PEGylated IL-11 (*200C/del P22), the platelet levels decreased less to an average of $362 \times 10^3$ cells/μL on day 5. Platelet levels in these animals returned to baseline levels by day 7. Similar results were seen in rats receiving 30 kDa-PEGylated IL-11 (*200C/del P22) and 40 kDa-PEGylated IL-11 (*200C/del P22). In animals that received these PEGylated IL-11 (*200C/del P22) proteins, platelet levels reached a nadir on day 5 and were back to normal pre-dose levels by day 7. In contrast, platelet levels did not return to baseline levels in the CPA+ vehicle control group until day 8. Platelet levels in animals receiving Neumega also did not return to baseline pre-dose levels until day 8. These results demonstrate the ability of the PEGylated IL-11 (*200C/del P22) proteins to reduce the severity of thrombocytopenia and to accelerate the recovery to normal platelet levels in myelosuppressed animals. The compound could also similarly be used to reduce the severity of thrombocytopenia and to accelerate the recovery to normal platelet levels in animals or humans rendered thrombocytopenic as result of other chemical treatments, radiological treatments, disease, drug treatments or idiopathic causes. Similar experiments can be performed using different dosing regimens such as every day, every third day and a single injection of the PEG-IL-11 proteins.

TABLE 11

Circulating platelet counts (expressed in thousands/μL) in animals receiving every other day subcutaneous injections of vehicle solution or 100 μg protein/kg of Neumega (IL-11), 20 kDa-PEG-IL11 (*200C/del P22), 30 kDa-PEG-IL11 (*200C/del P22) or 40 kDa-PEG-IL11 (*200C/del P22).

| Day | Vehicle (no CPA) | CPA + Vehicle | Neumega | CPA + 20 kDa-PEG *200C | CPA + 30 kDa-PEG *200C | CPA + 40 kDa-PEG *200C |
|---|---|---|---|---|---|---|
| −1 | 1012 ± 71 | 1017 ± 88 | 1025 ± 68 | 1025 ± 70 | 1012 ± 80 | 1011 ± 69 |
| 1 | 1002 ± 38 | 890 ± 58 | 929 ± 39 | 1070 ± 55 | 907 ± 45 | 988 ± 30 |
| 3 | 1006 ± 62 | 688 ± 32 | — | — | — | — |
| 5 | 1010 ± 48 | 306 ± 43 | 354 ± 19 | 362 ± 41 | 318 ± 12 | 376 ± 16 |

TABLE 11-continued

Circulating platelet counts (expressed in thousands/μL) in animals
receiving every other day subcutaneous injections of vehicle solution
or 100 μg protein/kg of Neumega (IL-11), 20 kDa-PEG-IL11 (*200C/del
P22), 30 kDa-PEG-IL11 (*200C/del P22) or 40 kDa-PEG-IL11 (*200C/del P22).

| Day | Vehicle (no CPA) | CPA + Vehicle | Neumega | CPA + 20 kDa-PEG *200C | CPA + 30 kDa-PEG *200C | CPA + 40 kDa-PEG *200C |
| --- | --- | --- | --- | --- | --- | --- |
| 6 | 988 ± 21 | 431 ± 92 | 562 ± 38 | 565 ± 51 | 570 ± 40 | 651 ± 25 |
| 7 | 1149 ± 42 | 753 ± 77 | 899 ± 42 | 1153 ± 68 | 1144 ± 45 | 1134 ± 72 |
| 8 | 989 ± 47 | 1165 ± 59 | 1133 ± 59 | 1175 ± 44 | 1206 ± 77 | 1374 ± 13 |
| 9 | 992 ± 35 | 1210 ± 64 | 1205 ± 57 | 1329 ± 78 | 1419 ± 21 | 1502 ± 73 |
| 10 | 995 ± 55 | 1255 ± 146 | 1178 ± 94 | 1843 ± 121 | 1770 ± 77 | 1883 ± 50 |
| 13 | 1022 ± 31 | 1469 ± 98 | 1363 ± 73 | 1549 ± 88 | 1543 ± 104 | 1411 ± 57 |

Control animals did not receive CPA but did receive every other day subcutaneous injections of vehicle solution. Data are means ± SEM.

Example 13

Cysteine Analogs can be Constructed at any Position of Interest in IL-11

Using the techniques and procedures disclosed in these Examples one of ordinary skill in the art could produce additional cysteine variants of IL-11 and purified PEGylated forms of cysteine variants of IL-11. The present inventor has determined that cysteine residues can potentially be substituted for any amino acid in IL-11. Cysteine substitution muteins can be prepared as described in the Examples and tested in the B9-11 cell proliferation assay to confirm they are biologically active. Biologically active IL-11 cysteine muteins can be reacted with cysteine reactive moieties such as cysteine reactive PEGs using procedures described in the Examples. The purified PEGylated cysteine muteins can be tested in the B9-11 cell proliferation assay to determine if they are biologically active. Biologically active cysteine muteins of IL-11 can be tested in animal models to determine if they stimulate hematopoiesis, and in particular thrombopoiesis and platelet formation, using the animal models described in the Examples. Multiple cysteine substitutions could also be constructed by combining two or more of the above cysteine muteins in one protein. Muteins containing more than one added cysteine can be used to create IL-11 proteins modified with more than one PEG.

Example 14

Other Methods for Preparing PEGylated Derivatives of IL-11 and IL-11 Analogs

PEGs can be attached to a peptide or protein through a variety of chemistries that target the amino acid side chains, the amino-terminal amino acid, the carboxy-terminal amino acid, or the sugar residues in the case of a glycosylated protein (See reviews by Veronese, 2001; Roberts et al., 2002; Morpurgo and Veronese, 2004). One preferred route for PEG conjugation of proteins is to use a PEG with a functional group that reacts with lysines and/or the N-terminal amino acid group. The literature describes more than a dozen such procedures (see reviews by Hooftman et al., 1996; Delgato et al., 1992; and Zalipsky, 1995). Examples of amine-reactive PEGs include PEG dichlorotriazine, PEG tresylate, PEG succinimidyl carbonate, PEG benzotriazole carbonate, PEG p-nitrophenyl carbonate, PEG carbonylimidazole, PEG succinimidyl succinate, PEG propionaldehyde, PEG acetaldehyde, and PEG hydroxysuccinimide The mature IL-11 protein has 3 lysine residues (K63, K120 and K196) in addition to the amino terminal amino acid available for conjugation with an amine-reactive PEG. Multiple attachments may occur if the protein is exposed to an excess amount of PEGylation reagent. Preferably, the IL-11 PEG conjugate would have 1-4 PEGs attached to the protein, more preferred would be 1-2 PEG attachments, and most preferred 1 PEG attachment. Conditions can be adjusted to limit the number of attachments or the site of PEG attachments. The number of attachments can be titrated by varying the molar ratios of the PEG:Protein. Preferred ratios can be determined experimentally. A second method for varying the number of PEG attachments is by modifying the reaction conditions. For example, the coupling can be preferentially directed to the alpha-terminus of a protein chain by performing the reaction at a pH lower than 7 and preferably below 6.5. Above pH 8, the epsilon-NH3 groups found on the lysines will be most reactive with the PEG reagent (Morpurgo and Veronese, 2004). A third approach to controlling the number or location of the PEG conjugates is to conduct the PEGylation in the presence of a substrate, reversible inhibitor, binding protein or soluble receptor such as a soluble IL-11 receptor so that the amino acids required for activity are protected during the PEG coupling reaction. A fourth approach to controlling the number of attachments involves using a larger PEG. For example when interferon-alpha is modified with a small linear PEG polymer, up to 11 positional isomers are present in the final mixture. When interferon-alpha is modified with a larger 40 kDa branched PEG, only four main positional isomers are present in the mono-PEGylated protein (Monkarsh et al., 1997, Foser et al. 2003, Bailon et al. 2003). A fifth method to control the number of attached PEGs is to use column chromatography procedures (including but not limited to ion exchange, size exclusion or hydrophobic interaction) to purify a IL-11 conjugate containing the desired number of PEG molecules from a more complex IL-11-PEG mixture. A six method to control the number of attached PEGs is to genetically modify the protein to reduce or add lysine residues to the protein's primary sequence. For example IL-11 analogs can be constructed in which one or more of the lysine residues (K63, K120, K196) are changed to a non-lysine amino acid such as arginine. Alternatively, IL-11 muteins in which a lysine residue is substituted for a non-lysine amino acid in IL-11, or added preceding the first amino acid of the mature protein or following the last amino acid of the mature protein can be created using standard DNA mutagensis procedures.

PEG-hydrazide can be used to PEGylate the carboxyl groups in presence of N,N'-dicyclohexylcarbodiimide (DCC), or in presence of a water soluble coupling agent such as N-(-3-dimethylaminopropyl)-N'-ethylcarbodiimide hydrochloride (EDC). The carboxyl groups of a protein when activated with EDC at an acidic pH (pH 4.5-5) react readily with PEG-hydrazide, whereas amino groups of the protein are protonated and unreactive.

Similar to the genetically engineered cysteine mutations for site specific PEGylation, researchers have reported the specific incorporation of unnatural amino acids into proteins expressed in yeast (Deiters et al., 2004). Specifically para-azidophenylalanine was substituted into a protein at certain sites determined by the positioning of the amber codon. The reactive group on the amino acid analog was used in a mild [3+2] cycloaddition reaction with an alkyne derivatized PEG reagent to allow for site-specific conjugation. Similar procedures can be applied to IL-11 to create PEGylated IL-11 analogs. Preferred sites for introduction of non-natural amino acids into the IL-11 coding sequence that result in biologically active IL-11 analogs and PEGylated IL-11 analogs can be determined using the methods and assays taught in the various Examples.

Another method for PEGylation of IL-11 is the attachment of the PEG moiety on the arginine side chain using PEG-1-3-dioxo compounds such as PEG-phenylglioxate. Other amino acids such as histidines and lysines may be modified as well.

PEG-isocyante can be used to attach a PEG to a hydroxy group via a stable urethane linkage. The disadvantage of this approach is lack of specificity since it is also capable of reacting with amines. Thus, this reagent is more commonly used in PEGylation reactions involving polysaccharides or non-peptide drugs.

Oxidation of the carbohydrate residues or N-terminal serine or threonine is an alternative method for a site-specific PEGylation. Carbohydrate side chains can be oxidized with enzymes or chemically with sodium periodate to generate reactive aldehyde groups. These sites can be reacted with either PEG-hydrazide or PEG-amine to produce a reversible Schiff's base. These linkages are then reduced with sodium cyanoborohydride to a more stable alkyl hydrazide or in the case of the Schiff's base, a secondary amine. Multiple attachment sites are generated by this method but the PEG is localized on the carbohydrate chain rather than on the protein.

A similar approach takes advantage of an N-terminal serine or threonine. These amino acid residues can be converted by periodate oxidation to a glyoxylyl derivative which will also react with PEG-hydrazide or PEG-amine. IL-11 analogs containing an amino-terminal serine or threonine residue can be constructed using standard DNA mutagenesis procedures.

Another approach for PEGylation of proteins uses the enzyme transglutaminase to modify glutamine residues so they become reactive with alkylamine derivatives of PEG. (Sato 2002). Similar procedures can be used to create PEGylated derivatives of IL-11.

Example 16

N-terminal PEGylation of IL-11

Purified IL-11 del P22 prepared by expression of the protein in *E. coli* using the intein system was incubated at a concentration of 100 µg protein/mL with a 5- to 400-fold molar excess of a 5 kDa-amine-reactive PEG (5 kDa-methoxy-SPA-PEG, Shearwater Corporation) at pH 6.0 or pH 6.5 in 100 mM MES buffer for one hour at room temperature. Analysis of the reaction mixture by SDS-PAGE showed the presence of a mono-PEGylated IL-11 protein at PEG:protein molar ratios above 10-20× in the pH 6.0 samples. The PEG-IL-11 protein migrated with an approximate molecular mass of 33 kDa by SDS-PAGE. The mono-PEGylated IL-11 protein can be purified by column chromatography as described in the Examples. Both monoPEGylated and diPEGylated IL-11 protein was observed in the pH 6.5 samples. MonoPEGylated protein was predominant at molar ratios above 5×. DiPEGylated protein (apparent molecular mass of 45 kDa by SDS-PAGE) was apparent at molar ratios above 75×.

Example 17

Amine-PEGylation of IL-11

Purified IL-11 del P22 prepared by expression of the protein in *E. coli* using the intein system was incubated at a concentration of 100 µg protein/mL with a 5- to 400-fold molar excess of a 5 kDa-amine-reactive PEG (5 kDa-methoxy-SPA-PEG, Shearwater Corporation) at pH 8.0 in 100 mM MES buffer for one hour at room temperature. Analysis of the reaction mixture by SDS-PAGE showed the presence of mono-PEGylated IL-11 protein at PEG:protein molar ratios above 5×. Analysis of the reaction mixture by SDS-PAGE showed the presence of di-PEGylated IL-11 protein at PEG:protein molar ratios above 50-75×. The mono-PEGylated IL-11 protein migrated with an approximate molecular mass of 33 kDa by SDS-PAGE. The di-PEGylated IL-11 protein migrated with an approximate molecular weight of 45 kDa. The mono-PEGylated IL-11 protein and di-PEGylated IL-11 protein can be purified by column chromatography as described in the Examples. A variety of column chromatography procedures, including but not limited to size-exclusion column chromatography can be used to isolate mono-PEGylated protein from di-PEGylated protein.

Example 18

Additional Cysteine Muteins of IL-11

Using the methods and techniques described in the Examples above, additional cysteine muteins containing a single cysteine substitution (E38C, L39C, S74C, T77C, A114C, S117C, A148C, S165C) or cysteine muteins containing two different cysteine substitutions in the same region or in two different regions (P25C/T77C; P25C/S117C; P25C/S165C; P24C/P25C; D69C/T77C; A162C/S165C), were constructed in the human IL-11 gene and were expressed in *E. coli* or in an insect cell expression system. The muteins are listed in Tables 12 and 13. The reference to position numbers is made with regard to the IL-11 amino acid sequence with the signal sequence (SEQ ID NO:17).

Certain of the muteins described above were expressed in insect cells using a baculovirus expression system and tested for biological activity vs. a wild type IL-11 control in an in vitro cell-line based proliferation assay. Supernatants of baculovirus infected insect cell lysates were tested in the bioassay, and the IL-11 cysteine mutein or wild type IL-11 protein present in the lysate was quantitated by a commercially available (R & D Systems) IL-11 ELISA assay. Certain of the cysteine muteins were subsequently purified and quantitated using a Bradford dye binding assay. Other cysteine muteins were expressed in *E. coli* and purified. These latter muteins also were quantitated using a Bradford dye binding assay. The bioassay measures IL-11-stimulated proliferation of a derivative the B9 cell line that has been adapted to proliferate in response to IL-11. In this assay, all of the cysteine muteins described above (Tables 12 and 13) were biologically active. The EC50 (the concentration of protein resulting in one half the maximal stimulation of proliferation) of the muteins ranged from within 2-fold of the EC50 of the wild type IL-11 control to greater than 14-fold or 33-fold higher than the EC50 of the wild type control.

Several of the cysteine muteins listed in Table 12 and wild type IL-11 were purified to homogeneity from the supernatants of baculovirus infected insect cell lysates or from *E. coli* lysates, and these purified cysteine muteins were modified with polyethylene glycol ("PEGylated") using techniques described in the Examples above. The PEGylated forms of the cysteine muteins were purified away from any unmodified material. The purified cysteine muteins and the purified PEGylated cysteine muteins were assayed for biological activity vs. a wild type IL-11 control in the in vitro cell-line proliferation assay. All of the purified cysteine muteins and the purified PEGylated cysteine muteins were biologically active.

TABLE 12

In vitro bioactivities of Additional Cysteine Muteins of IL-11

| IL-11 Protein | EC50 (ng/mL) | Added cysteine location | EC50 with 20K-PEG |
|---|---|---|---|
| IL-11 (Neumega) | 3.2 +/− 0.9 | | |
| IL-11 | 3.3 +/− 0.6 | | |
| S74C | 44.3 +/− 13.1 | A-B loop | 345 +/− 21.2 |
| T77C | 5.6 +/− 0.1 | A-B loop | 14.3 +/− 0.5 |
| A114C | 11.5 +/− 0.6 | B-C loop | 19.3 +/− 1.5 |
| S117C | 12 +/− 0.8 | B-C loop | 13.8 +/− 0.5 |
| A148C | 8 +/− 0.4 | C-D loop | |
| S165C | 9.8 +/− 2 | C-D loop | 7.6 +/− 1.1 |

IL-11 positions are relative to SEQ ID NO: 17

TABLE 13

In vitro bioactivities of Additional Cysteine Muteins of IL-11

| IL-11 Protein | EC50 (ng/ml) by Assay | | | | | | | |
|---|---|---|---|---|---|---|---|---|
| | #1 | #2 | #3 | #4 | #5 | #6 | #7 | #8 |
| IL-11 | 6.3 | 6.3 | 5.1 | 5.3 | 6.3 | 6.1 | 7 | 6 |
| IL-11 (E38C) | | | 7.1 | 7.1 | | | | |
| IL-11 (L39C) | | | ~200 | ~200 | | | | |
| IL-11 (P25C/T77C) | 6.1 | 6.1 | | | | | | |
| IL-11 (P25C/S117C) | 7.1 | 9.1 | | | | | | |
| IL-11 (P25C/S165C) | | | | | 6.3 | 5.8 | | |
| IL-11 (P24C/P25C) | | | | | 5.3 | 6 | | |
| IL-11 (D69C/T77C) | | | | | | | 5.2 | 6 |
| IL-11 (A162C/S165C) | | | | | | | 6 | 5 |

IL-11 positions are relative to SEQ ID NO: 17

REFERENCES

Bailon P, Palleroni A, Schaffer C A, Spence C L, Fung W J, Porter J E, Ehrlich G K, Pan W, Xu Z X, Modi M W, Farid A, Berthold W, Graves M. (2001) Bioconjug Chem. 12(2): 195-202. Rational design of a potent, long-lasting form of interferon: a 40 kDa branched polyethylene glycol-conjugated interferon alpha-2a for the treatment of hepatitis C.

Cairo M S (2000) Dose reductions and delays: limitations of myelosuppressive chemotherapy. Oncology 14: 21-31.

Delgado, C. Francis, G E, and Derek (1992) Critical Rev Ther Drug Carrier Sys 9:249-304. The uses and properties of PEG-linked proteins.

Dieterich D T, Spivak J L (2003) Hematologic disorders associated with hepatitis C virus infection and their management. Clin Infect Dis 37: 533-541.

Deiters, A., Cropp, T. A., Summerer D., Mukherji M. and Schultz, P. G. (2004) Bioorg. Med. Chem. Lett. 14: 5743-5745.

Foser S, Schacher A, Weyer K A, Brugger D, Dietel E, Marti S, Schreitmuller T. (2003) Protein Expr Purif. 30(1):78-87. Isolation, structural characterization, and antiviral activity of positional isomers of monopegylated interferon alpha-2a (PEGASYS).

Ghalib R, Levine C, Hassan M, McClelland T, Goss J, Stribling R, Seu P, Patt YZ (2003) Recombinant human interleukin-11 improves thrombocytopenia in patients with cirrhosis. Hepatology 37: 1165-1171.

Gordon, M S (1999) Advances in supportive care of myelodysplatic syndromes. Semin Hematol 36: 21-24.

Hooftman, G. Herman, S., Schacht, E. (1996) J. Bioactive Compatible Polymer 11:135-139. PEGs with reactive end-groups II. Practical considerations for the preparation of protein-PEG conjugates.

Horton, R. M. (1993) In vitro Recombination and mutagnesis of DNA. SOIng together tailor-made genes. *Methods in Molecular Biology*, Vol. 15: *PCR Protocols: Current Methods and Applications* (B. A. White, Ed.) pp 251-2266, Chapter 25, Humana Press, Totawa, N.J.

Kurzrock R, Cortes J, Thomas D A, Jeha S, Pilat S, Talpaz M (2001) Pilot study of low-dose interleukin-11 in patients with bone marrow failure. J Clin Oncol 19: 4165-4172.

McKinley, D., Wu, Q., Yang-Feng, T., and Yang, Y. C. (1992) Genomics 13: 814-819.

Monkarsh, S P, Ma, Y, Aglione, A, Bailon, P, Ciolek, D, DeBarbieri, B, Graves, M C, Hollfelder, K, Michel, H, Palleroni A, Porter, J E, Russoman, E, Roy, S, and Pan Y C. (1997) Anal Biochem. 247(2):434-440. Positional isomers of monopegylated interferon alpha: isolation, characterization, and biological activity.

Morpurgo, M. and Veronese, F. (2004) in Methods in Molecular Biology 283: 45-70. Conjugates of Peptides and Proteins to Polyethylene Glycols.

Ramasethu J (2004) Thrombocytopenia in the newborn. Curr Hematol Rep 3: 134-142.

Ranjan A, Hasnain SE. Influence of codon usage and translation initiation codon context in the AcNPV-based expression system: computer analysis using homologous and heterologous genes. Virus Genes. 1995; 9: 149-153.

Roberts, M. J. Bentley, M. and Harris, J. M. (2002) Advanced Drug Delivery Reviews. 54:459-476. Chemistry for peptide and protein PEGylation.

Sato, H. (2002) Adv. Drug Deliv. Rev 54:487-509. Enzymatic procedure for site-specific PEGylation of proteins.

Scharf, S. J., (1990) Cloning with PCR. *PCR Protocols: A Guide to Methods and Applications*. (Innis, M. A., Gelfand, D. H, Sninsky, J. J. and White, T. J. Eds.) pp 84-91. Chapter 11, Academic Press, San Diego, Calif.

Tsimberidou A M, Giles F J, Khouri I, Bueso-Ramos C, Pilat S, Thomas D A, Cortes J, Kurzrock R (2005) Low-dose interleukin-11 in patients with bone marrow failure: update of the M.D. Anderson Cancer Center experience. Ann Oncol 16: 139-145.

Veronese, F. (2001) Biomaterials 22:405-417. Peptide and protein PEGylation: a review of problems and solutions.

Yamamoto Y, Tsutsumi Y, Yoshioka Y, Nishibata T, Kobayashi K, Okamoto T, Mukai Y, Shimizu T, Nakagawa S, Nagata S, Mayumi T. (2003) Nat. Biotechnol. 21(5):546-52. Site-specific PEGylation of a lysine-deficient TNF-alpha with full bioactivity.

Zalispky, C. (1995) Adv. Drug Delivery Rev 16:157-182.

All of the documents cited herein are incorporated herein by reference.

The protein analogues (i.e., the cysteine variants or muteins) disclosed herein can be used for the known therapeutic uses of the native proteins in essentially the same forms and doses all well known in the art.

While the exemplary preferred embodiments of the present invention are described herein with particularity, those having ordinary skill in the art will recognize changes, modifications, additions, and applications other than those specifically described herein, and may adapt the preferred embodiments and methods without departing from the spirit of this invention.

What is claimed is:

1. A method to treat an animal with a disease or condition that can be treated by wild-type interleukin-11 (IL-11), to stimulate platelet production in an animal, or to accelerate an animal's recovery from thrombocytopenia, comprising administering to the animal an effective amount of interleukin-11 (IL-11) cysteine mutein, wherein the mutein comprises (a) at least one cysteine residue substituted for an amino acid in IL-11 (SEQ ID NO:17) selected from the group consisting of: P22, G23, P24, G27, and A162;

(b) at least one cysteine residue substituted for an amino acid in IL-11 (SEQ ID NO:17) selected from the group consisting of: P24, P25, E38, L39, D69, L72, S74, T77, A114, S117, E123, A148, and S165, and further comprises deletion of amino acid P22 in IL-11 (SEQ ID NO:17);

(c) at least one non-native cysteine residue which has been added following the C-terminal amino acid of IL-11 (SEQ ID NO:17);

(d) at least one non-native cysteine residue which has been added following the C-terminal amino acid of IL-11 (SEQ ID NO:17), and further comprises deletion of amino acid P22 in IL-11 (SEQ ID NO:17);

(e) deletion of one or more amino acids in IL-11 (SEQ ID NO:17) selected from the group consisting of: deletion of amino acid P22, deletion of amino acids 22-26 and deletion of amino acids 22-29; or (f) at least two cysteine substitutions, wherein a cysteine residue is substituted for an amino acid in IL-11 (SEQ ID NO:17) selected from the group consisting of P25 and T77, P25 and S117, P25 and S165, P25 and P24, D69 and T77 and A162 and S165 and further comprises deletion of amino acid P22 in IL-11 (SEQ ID NO:17); and wherein the mutein has biological activity in vitro as measured by proliferation of a cell line that proliferates in response to IL-11.

2. The method of claim 1, wherein the thrombocytopenia is selected from the group consisting of: (a) thrombocytopenia resulting from myelosuppressive chemotherapy; (b) thrombocytopenia resulting from other chemical treatments; (c) thrombocytopenia resulting from radiological treatments; (d) thrombocytopenia resulting from disease; (e) thrombocytopenia resulting from idiopathic causes; (f) thrombocytopenia resulting from drug treatments, including interferons and ribavarin; (g) thrombocytopenia in neonates; (h) thrombocytopenia resulting from myelodysplastic syndromes; (i) thrombocytopenia resulting from aplastic anemia; and (j) thrombocytopenia resulting from cirrhosis.

3. The method of claim 1, wherein the thrombocytopenia is thrombocytopenia resulting from myelosuppressive chemotherapy.

4. The method of claim 1, wherein the cysteine mutein is modified with at least one polyethylene glycol.

5. The method of claim 1, wherein the IL-11 cysteine mutein is modified with a cysteine-reactive moiety.

6. The method of claim 5, wherein the cysteine-reactive moiety is a polyethylene glycol.

7. The method of claim 1, wherein the cysteine mutein is administered by a route selected from the group consisting of intravenous administration, intraperitoneal administration, intramuscular administration, intranodal administration, intracoronary administration, intraarterial administration, subcutaneous administration, transdermal delivery, intratracheal administration, intraarticular administration, intraventricular administration, inhalation, intranasal, intracranial, intraspinal, intraocular, aural, oral, pulmonary administration, impregnation of a catheter, and direct injection into a tissue.

* * * * *

SEQUENCE LISTING

```
<160> NUMBER OF SEQ ID NOS: 52

<210> SEQ ID NO 1
<211> LENGTH: 191
<212> TYPE: PRT
<213> ORGANISM: Homo sapiens

<400> SEQUENCE: 1

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
        50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
                100                 105                 110

Leu Leu Lys Asp Leu Glu Glu Gly Ile Gln Thr Leu Met Gly Arg Leu
            115                 120                 125

Glu Asp Gly Ser Pro Arg Thr Gly Gln Ile Phe Lys Gln Thr Tyr Ser
        130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 2
<211> LENGTH: 166
<212> TYPE: PRT
<213> ORGANISM: Homo sapiens

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60
```

```
Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 3
<211> LENGTH: 165
<212> TYPE: PRT
<213> ORGANISM: Homo sapiens

<400> SEQUENCE: 3

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 4
<211> LENGTH: 166
<212> TYPE: PRT
<213> ORGANISM: Homo sapiens

<400> SEQUENCE: 4

Cys Asp Leu Pro Glu Thr His Ser Leu Asp Asn Arg Arg Thr Leu Met
1               5                   10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45
```

```
Gln Lys Ala Pro Ala Ile Ser Val Leu His Glu Leu Ile Gln Gln Ile
 50                  55                  60

Phe Asn Leu Phe Thr Thr Lys Asp Ser Ser Ala Ala Trp Asp Glu Asp
 65                  70                  75                  80

Leu Leu Asp Lys Phe Cys Thr Glu Leu Tyr Gln Gln Leu Asn Asp Leu
                 85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 5
<211> LENGTH: 166
<212> TYPE: PRT
<213> ORGANISM: Homo sapiens

<400> SEQUENCE: 5

Met Ser Tyr Asn Leu Leu Gly Phe Leu Gln Arg Ser Ser Asn Phe Gln
 1                   5                  10                  15

Cys Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 6
<211> LENGTH: 174
<212> TYPE: PRT
<213> ORGANISM: Homo sapiens

<400> SEQUENCE: 6

Thr Pro Leu Gly Pro Ala Ser Ser Leu Pro Gln Ser Phe Leu Leu Lys
 1                   5                  10                  15

Cys Leu Glu Gln Val Arg Lys Ile Gln Gly Asp Gly Ala Ala Leu Gln
                20                  25                  30
```

```
Glu Lys Leu Cys Ala Thr Tyr Lys Leu Cys His Pro Glu Leu Val
         35                  40                  45

Leu Leu Gly His Ser Leu Gly Ile Pro Trp Ala Pro Leu Ser Ser Cys
 50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
                100                 105                 110

Phe Ala Thr Thr Ile Trp Gln Gln Met Glu Glu Leu Gly Met Ala Pro
                115                 120                 125

Ala Leu Gln Pro Thr Gln Gly Ala Met Pro Ala Phe Ala Ser Ala Phe
            130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

<210> SEQ ID NO 7
<211> LENGTH: 332
<212> TYPE: PRT
<213> ORGANISM: Homo sapiens

<400> SEQUENCE: 7

```
Ser Pro Ala Pro Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
                 20                  25                  30

His Pro Leu Pro Thr Pro Val Leu Leu Pro Ala Val Asp Phe Ser Leu
                 35                  40                  45

Gly Glu Trp Lys Thr Gln Met Glu Glu Thr Lys Ala Gln Asp Ile Leu
             50                  55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
            115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu Pro Asn
                165                 170                 175

Arg Thr Ser Gly Leu Leu Glu Thr Asn Phe Thr Ala Ser Ala Arg Thr
                180                 185                 190

Thr Gly Ser Gly Leu Leu Lys Trp Gln Gln Gly Phe Arg Ala Lys Ile
            195                 200                 205

Pro Gly Leu Leu Asn Gln Thr Ser Arg Ser Leu Asp Gln Ile Pro Gly
210                 215                 220

Tyr Leu Asn Arg Ile His Glu Leu Leu Asn Gly Thr Arg Gly Leu Phe
225                 230                 235                 240
```

```
Pro Gly Pro Ser Arg Arg Thr Leu Gly Ala Pro Asp Ile Ser Ser Gly
            245                 250                 255

Thr Ser Asp Thr Gly Ser Leu Pro Pro Asn Leu Gln Pro Gly Tyr Ser
            260                 265                 270

Pro Ser Pro Thr His Pro Pro Thr Gly Gly Tyr Thr Leu Phe Pro Leu
            275                 280                 285

Pro Pro Thr Leu Pro Thr Pro Val Val Gln Leu His Pro Leu Leu Pro
            290                 295                 300

Asp Pro Ser Ala Pro Thr Pro Thr Pro Thr Ser Pro Leu Leu Asn Thr
305                 310                 315                 320

Ser Tyr Thr His Ser Gln Asn Leu Ser Gln Glu Gly
            325                 330

<210> SEQ ID NO 8
<211> LENGTH: 127
<212> TYPE: PRT
<213> ORGANISM: Homo sapiens

<400> SEQUENCE: 8

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
            35                  40                  45

Leu Gln Glu Pro Thr Cys Leu Gln Thr Arg Leu Glu Leu Tyr Lys Gln
        50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
            115                 120                 125

<210> SEQ ID NO 9
<211> LENGTH: 133
<212> TYPE: PRT
<213> ORGANISM: Homo sapiens

<400> SEQUENCE: 9

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110
```

-continued

```
Thr Ile Val Glu Phe Leu Asn Arg Trp Ile Thr Phe Cys Gln Ser Ile
        115                 120                 125
Ile Ser Thr Leu Thr
    130

<210> SEQ ID NO 10
<211> LENGTH: 152
<212> TYPE: PRT
<213> ORGANISM: Homo sapiens

<400> SEQUENCE: 10

Met Ser Arg Leu Pro Val Leu Leu Leu Gln Leu Leu Val Arg Pro
1               5                   10                  15

Gly Leu Gln Ala Pro Met Thr Gln Thr Thr Pro Leu Lys Thr Ser Trp
            20                  25                  30

Val Asn Cys Ser Asn Met Ile Asp Glu Ile Ile Thr His Leu Lys Gln
        35                  40                  45

Pro Pro Leu Pro Leu Leu Asp Phe Asn Asn Leu Asn Gly Glu Asp Gln
    50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe
145                 150

<210> SEQ ID NO 11
<211> LENGTH: 129
<212> TYPE: PRT
<213> ORGANISM: Homo sapiens

<400> SEQUENCE: 11

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser

<210> SEQ ID NO 12
```

```
<211> LENGTH: 134
<212> TYPE: PRT
<213> ORGANISM: Homo sapiens

<400> SEQUENCE: 12

Met Arg Met Leu Leu His Leu Ser Leu Ala Leu Gly Ala Ala Tyr
1               5                   10                  15

Val Tyr Ala Ile Pro Thr Glu Ile Pro Thr Ser Ala Leu Val Lys Glu
            20                  25                  30

Thr Leu Ala Leu Leu Ser Thr His Arg Thr Leu Leu Ile Ala Asn Glu
                35                  40                  45

Thr Leu Arg Ile Pro Val Pro Val His Lys Asn His Gln Leu Cys Thr
50                  55                  60

Glu Glu Ile Phe Gln Gly Ile Gly Thr Leu Glu Ser Gln Thr Val Gln
65                  70                  75                  80

Gly Gly Thr Val Glu Arg Leu Phe Lys Asn Leu Ser Leu Ile Lys Lys
                85                  90                  95

Tyr Ile Asp Gly Gln Lys Lys Cys Gly Glu Arg Arg Val
            100                 105                 110

Asn Gln Phe Leu Asp Tyr Leu Gln Glu Phe Leu Gly Val Met Asn Thr
            115                 120                 125

Glu Trp Ile Ile Glu Ser
        130

<210> SEQ ID NO 13
<211> LENGTH: 212
<212> TYPE: PRT
<213> ORGANISM: Homo sapiens

<400> SEQUENCE: 13

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Glu Gln Ala Arg Ala Val Gln
            130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
            195                 200                 205
```

```
Leu Arg Gln Met
    210

<210> SEQ ID NO 14
<211> LENGTH: 177
<212> TYPE: PRT
<213> ORGANISM: Homo sapiens

<400> SEQUENCE: 14

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 15
<211> LENGTH: 144
<212> TYPE: PRT
<213> ORGANISM: Homo sapiens

<400> SEQUENCE: 15

Met Leu Leu Ala Met Val Leu Thr Ser Ala Leu Leu Cys Ser Val
1               5                   10                  15

Ala Gly Gln Gly Cys Pro Thr Leu Ala Gly Ile Leu Asp Ile Asn Phe
            20                  25                  30

Leu Ile Asn Lys Met Gln Glu Asp Pro Ala Ser Lys Cys His Cys Ser
        35                  40                  45

Ala Asn Val Thr Ser Cys Leu Cys Leu Gly Ile Pro Ser Asp Asn Cys
    50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
                85                  90                  95

Glu Val Leu Lys Asn Asn Lys Cys Pro Tyr Phe Ser Cys Glu Gln Pro
            100                 105                 110

Cys Asn Gln Thr Thr Ala Gly Asn Ala Leu Thr Phe Leu Lys Ser Leu
        115                 120                 125

Leu Glu Ile Phe Gln Lys Glu Lys Met Arg Gly Met Arg Gly Lys Ile
    130                 135                 140
```

```
<210> SEQ ID NO 16
<211> LENGTH: 178
<212> TYPE: PRT
<213> ORGANISM: Homo sapiens

<400> SEQUENCE: 16

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 17
<211> LENGTH: 199
<212> TYPE: PRT
<213> ORGANISM: Homo sapiens

<400> SEQUENCE: 17

Met Asn Cys Val Cys Arg Leu Val Leu Val Val Leu Ser Leu Trp Pro
1               5                   10                  15

Asp Thr Ala Val Ala Pro Gly Pro Pro Gly Pro Pro Arg Val Ser
            20                  25                  30

Pro Asp Pro Arg Ala Glu Leu Asp Ser Thr Val Leu Leu Thr Arg Ser
        35                  40                  45

Leu Leu Ala Asp Thr Arg Gln Leu Ala Ala Gln Leu Arg Asp Lys Phe
    50                  55                  60

Pro Ala Asp Gly Asp His Asn Leu Asp Ser Leu Pro Thr Leu Ala Met
65                  70                  75                  80

Ser Ala Gly Ala Leu Gly Ala Leu Gln Leu Pro Gly Val Leu Thr Arg
                85                  90                  95

Leu Arg Ala Asp Leu Leu Ser Tyr Leu Arg His Val Gln Trp Leu Arg
            100                 105                 110

Arg Ala Gly Gly Ser Ser Leu Lys Thr Leu Glu Pro Glu Leu Gly Thr
        115                 120                 125

Leu Gln Ala Arg Leu Asp Arg Leu Leu Arg Arg Leu Gln Leu Leu Met
    130                 135                 140
```

```
Ser Arg Leu Ala Leu Pro Gln Pro Pro Asp Pro Ala Pro Pro
145                 150                 155                 160

Leu Ala Pro Pro Ser Ala Trp Gly Gly Ile Arg Ala Ala His Ala
            165                 170                 175

Ile Leu Gly Gly Leu His Leu Thr Leu Asp Trp Ala Val Arg Gly Leu
        180                 185                 190

Leu Leu Leu Lys Thr Arg Leu
            195

<210> SEQ ID NO 18
<211> LENGTH: 219
<212> TYPE: PRT
<213> ORGANISM: Homo sapiens

<400> SEQUENCE: 18

Met Cys Pro Ala Arg Ser Leu Leu Val Ala Thr Leu Val Leu Leu
1               5                   10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Pro Cys
50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Thr Ser Tyr Leu Asn Ala Ser
210                 215

<210> SEQ ID NO 19
<211> LENGTH: 132
<212> TYPE: PRT
<213> ORGANISM: Homo sapiens

<400> SEQUENCE: 19

Met Ala Leu Leu Leu Thr Thr Val Ile Ala Leu Thr Cys Leu Gly Gly
1               5                   10                  15

Phe Ala Ser Pro Gly Pro Val Pro Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45
```

```
Asn Gly Ser Met Val Trp Ser Ile Asn Leu Thr Ala Gly Met Tyr Cys
        50                  55                  60

Ala Ala Leu Glu Ser Leu Ile Asn Val Ser Gly Cys Ser Ala Ile Glu
65                      70                  75                  80

Lys Thr Gln Arg Met Leu Ser Gly Phe Cys Pro His Lys Val Ser Ala
                    85                  90                  95

Gly Gln Phe Ser Ser Leu His Val Arg Asp Thr Lys Ile Glu Val Ala
                100                 105                 110

Gln Phe Val Lys Asp Leu Leu His Leu Lys Lys Leu Phe Arg Glu
                115                 120                 125

Gly Arg Phe Asn
        130

<210> SEQ ID NO 20
<211> LENGTH: 114
<212> TYPE: PRT
<213> ORGANISM: Homo sapiens

<400> SEQUENCE: 20

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                      70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 21
<211> LENGTH: 252
<212> TYPE: PRT
<213> ORGANISM: Homo sapiens

<400> SEQUENCE: 21

Met Gly Val Leu Leu Thr Gln Arg Thr Leu Leu Ser Leu Val Leu Ala
1               5                   10                  15

Leu Leu Phe Pro Ser Met Ala Ser Met Ala Ala Ile Gly Ser Cys Ser
                20                  25                  30

Lys Glu Tyr Arg Val Leu Leu Gly Gln Leu Gln Lys Gln Thr Asp Leu
            35                  40                  45

Met Gln Asp Thr Ser Arg Leu Leu Asp Pro Tyr Ile Arg Ile Gln Gly
        50                  55                  60

Leu Asp Val Pro Lys Leu Arg Glu His Cys Arg Glu Arg Pro Gly Ala
65                      70                  75                  80

Phe Pro Ser Glu Glu Thr Leu Arg Gly Leu Gly Arg Arg Gly Phe Leu
                85                  90                  95

Gln Thr Leu Asn Ala Thr Leu Gly Cys Val Leu His Arg Leu Ala Asp
                100                 105                 110

Leu Glu Gln Arg Leu Pro Lys Ala Gln Asp Leu Glu Arg Ser Gly Leu
                115                 120                 125
```

```
Asn Ile Glu Asp Leu Glu Lys Leu Gln Met Ala Arg Pro Asn Ile Leu
            130                 135                 140

Gly Leu Arg Asn Asn Ile Tyr Cys Met Ala Gln Leu Leu Asp Asn Ser
145                 150                 155                 160

Asp Thr Ala Glu Pro Thr Lys Ala Gly Arg Gly Ala Ser Gln Pro Pro
                165                 170                 175

Thr Pro Thr Pro Ala Ser Asp Ala Phe Gln Arg Lys Leu Glu Gly Cys
            180                 185                 190

Arg Phe Leu His Gly Tyr His Arg Phe Met His Ser Val Gly Arg Val
                195                 200                 205

Phe Ser Lys Trp Gly Glu Ser Pro Asn Arg Ser Arg Arg His Ser Pro
210                 215                 220

His Gln Ala Leu Arg Lys Gly Val Arg Arg Thr Arg Pro Ser Arg Lys
225                 230                 235                 240

Gly Lys Arg Leu Met Thr Arg Gly Gln Leu Pro Arg
                245                 250

<210> SEQ ID NO 22
<211> LENGTH: 200
<212> TYPE: PRT
<213> ORGANISM: Homo sapiens

<400> SEQUENCE: 22

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
                20                  25                  30

Ala Leu Thr Glu Ser Tyr Val Lys His Gln Gly Leu Asn Lys Asn Ile
            35                  40                  45

Asn Leu Asp Ser Ala Asp Gly Met Pro Val Ala Ser Thr Asp Gln Trp
50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
        130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200

<210> SEQ ID NO 23
<211> LENGTH: 181
<212> TYPE: PRT
<213> ORGANISM: Homo sapiens

<400> SEQUENCE: 23
```

-continued

```
Ser Pro Leu Pro Ile Thr Pro Val Asn Ala Thr Cys Ala Ile Arg His
1               5                   10                  15

Pro Cys His Asn Asn Leu Met Asn Gln Ile Arg Ser Gln Leu Ala Gln
            20                  25                  30

Leu Asn Gly Ser Ala Asn Ala Leu Phe Ile Leu Tyr Tyr Thr Ala Gln
            35                  40                  45

Gly Glu Pro Phe Pro Asn Asn Leu Asp Lys Leu Cys Gly Pro Asn Val
            50                  55                  60

Thr Asp Phe Pro Pro Phe His Ala Asn Gly Thr Glu Lys Ala Lys Leu
65                  70                  75                  80

Val Glu Leu Tyr Arg Ile Val Val Tyr Leu Gly Thr Ser Leu Gly Asn
                85                  90                  95

Ile Thr Arg Asp Gln Lys Ile Leu Asn Pro Ser Ala Leu Ser Leu His
            100                 105                 110

Ser Lys Leu Asn Ala Thr Ala Asp Ile Leu Arg Gly Leu Leu Ser Asn
            115                 120                 125

Val Leu Cys Arg Leu Cys Ser Lys Tyr His Val Gly His Val Asp Val
            130                 135                 140

Thr Tyr Gly Pro Pro Asp Thr Ser Gly Lys Asp Val Phe Gln Lys Lys
145                 150                 155                 160

Lys Leu Gly Cys Gln Leu Leu Gly Lys Tyr Lys Gln Ile Ile Ala Val
                165                 170                 175

Leu Ala Gln Ala Phe
            180

<210> SEQ ID NO 24
<211> LENGTH: 29
<212> TYPE: DNA
<213> ORGANISM: Artificial
<220> FEATURE:
<223> OTHER INFORMATION: primer

<400> SEQUENCE: 24
catatgttcc caaccattcc cttatccag                                     29

<210> SEQ ID NO 25
<211> LENGTH: 33
<212> TYPE: DNA
<213> ORGANISM: Artificial
<220> FEATURE:
<223> OTHER INFORMATION: primer

<400> SEQUENCE: 25
gggggatcct cactagaagc cacagctgcc ctc                                33

<210> SEQ ID NO 26
<211> LENGTH: 39
<212> TYPE: DNA
<213> ORGANISM: Artificial
<220> FEATURE:
<223> OTHER INFORMATION: primer

<400> SEQUENCE: 26
ccccggatcc gccaccatgg atctctggca gctgctgtt                          39

<210> SEQ ID NO 27
<211> LENGTH: 40
<212> TYPE: DNA
<213> ORGANISM: Artificial
<220> FEATURE:
<223> OTHER INFORMATION: primer
```

-continued

<400> SEQUENCE: 27
ccccgtcgac tctagagcta ttaaatacgt agctcttggg                                40

<210> SEQ ID NO 28
<211> LENGTH: 32
<212> TYPE: DNA
<213> ORGANISM: Artificial
<220> FEATURE:
<223> OTHER INFORMATION: primer

<400> SEQUENCE: 28
cgcggatccg attagaatcc acagctcccc tc                                        32

<210> SEQ ID NO 29
<211> LENGTH: 66
<212> TYPE: DNA
<213> ORGANISM: Artificial
<220> FEATURE:
<223> OTHER INFORMATION: primer

<400> SEQUENCE: 29 cccctctag acatatgaag aagaacatcg cattcctgct ggcatctatg ttcgttttct           60
ctatcg                                                                     66

<210> SEQ ID NO 30
<211> LENGTH: 65
<212> TYPE: DNA
<213> ORGANISM: Artificial
<220> FEATURE:
<223> OTHER INFORMATION: primer

<400> SEQUENCE: 30
gcatctatgt tcgttttctc tatcgctacc aacgcttacg cattcccaac cattcccta          60 tccag                                                                      65

<210> SEQ ID NO 31
<211> LENGTH: 62
<212> TYPE: DNA
<213> ORGANISM: Artificial
<220> FEATURE:
<223> OTHER INFORMATION: primer

<400> SEQUENCE: 31
gcagtggcac tggctggttt cgctaccgta gcgcaggcct cccaaccat tccttatcc           60 ag                                                                         62

<210> SEQ ID NO 32
<211> LENGTH: 59
<212> TYPE: DNA
<213> ORGANISM: Artificial
<220> FEATURE:
<223> OTHER INFORMATION: primer

<400> SEQUENCE: 32
ccccgtcgac acatatgaag aagacagcta tcgcgattgc agtggcactg gctggtttc          59

<210> SEQ ID NO 33
<211> LENGTH: 36
<212> TYPE: DNA
<213> ORGANISM: Artificial
<220> FEATURE:
<223> OTHER INFORMATION: primer

<400> SEQUENCE: 33

-continued

```
ctgcttgaag atctgcccac accgggggct gccatc                                    36
```

<210> SEQ ID NO 34
<211> LENGTH: 24
<212> TYPE: DNA
<213> ORGANISM: Artificial
<220> FEATURE:
<223> OTHER INFORMATION: primer

<400> SEQUENCE: 34

```
gtagcgcagg ccttcccaac catt                                                 24
```

<210> SEQ ID NO 35
<211> LENGTH: 39
<212> TYPE: DNA
<213> ORGANISM: Artificial
<220> FEATURE:
<223> OTHER INFORMATION: primer

<400> SEQUENCE: 35

```
ctgcttgaag atctgcccag tccggggggca gccatcttc                                39
```

<210> SEQ ID NO 36
<211> LENGTH: 51
<212> TYPE: DNA
<213> ORGANISM: Artificial
<220> FEATURE:
<223> OTHER INFORMATION: primer

<400> SEQUENCE: 36

```
gggcagatct tcaagcagac ctacagcaag ttcgactgca actcacacaa c                   51
```

<210> SEQ ID NO 37
<211> LENGTH: 34
<212> TYPE: DNA
<213> ORGANISM: Artificial
<220> FEATURE:
<223> OTHER INFORMATION: primer

<400> SEQUENCE: 37

```
cgcggtaccc gggatccgat tagaatccac agct                                      34
```

<210> SEQ ID NO 38
<211> LENGTH: 36
<212> TYPE: DNA
<213> ORGANISM: Artificial
<220> FEATURE:
<223> OTHER INFORMATION: primer

<400> SEQUENCE: 38

```
gggcagatct tcaagcagac ctactgcaag ttcgac                                    36
```

<210> SEQ ID NO 39
<211> LENGTH: 42
<212> TYPE: DNA
<213> ORGANISM: Artificial
<220> FEATURE:
<223> OTHER INFORMATION: primer

<400> SEQUENCE: 39

```
cgcggtaccg gatccttagc agaagccaca gctgccctcc ac                             42
```

<210> SEQ ID NO 40
<211> LENGTH: 24
<212> TYPE: DNA
<213> ORGANISM: Artificial
<220> FEATURE:

```
<223> OTHER INFORMATION: primer

<400> SEQUENCE: 40
gtagcgcagg ccttcccaac catt                                           24

<210> SEQ ID NO 41
<211> LENGTH: 40
<212> TYPE: DNA
<213> ORGANISM: Artificial
<220> FEATURE:
<223> OTHER INFORMATION: primer

<400> SEQUENCE: 41
ccccgtcgac tctagagcca ttagatacaa agctcttggg                          40

<210> SEQ ID NO 42
<211> LENGTH: 36
<212> TYPE: DNA
<213> ORGANISM: artificial
<220> FEATURE:
<223> OTHER INFORMATION: primer

<400> SEQUENCE: 42
cgcaagcttg ccaccatgaa ctgtgtttgc cgcctg                              36

<210> SEQ ID NO 43
<211> LENGTH: 30
<212> TYPE: DNA
<213> ORGANISM: Artificial
<220> FEATURE:
<223> OTHER INFORMATION: primer

<400> SEQUENCE: 43
gcgggacatc aggagctgca gccggcgcag                                     30

<210> SEQ ID NO 44
<211> LENGTH: 27
<212> TYPE: DNA
<213> ORGANISM: Artificial
<220> FEATURE:
<223> OTHER INFORMATION: primer

<400> SEQUENCE: 44
cagctcctga tgtcccgcct ggccctg                                        27

<210> SEQ ID NO 45
<211> LENGTH: 27
<212> TYPE: DNA
<213> ORGANISM: Artificial
<220> FEATURE:
<223> OTHER INFORMATION: primer

<400> SEQUENCE: 45
agtcttcagc agcagcagtc ccctcac                                        27

<210> SEQ ID NO 46
<211> LENGTH: 35
<212> TYPE: DNA
<213> ORGANISM: Artificial
<220> FEATURE:
<223> OTHER INFORMATION: primer

<400> SEQUENCE: 46
cgcggatcct ccgacagccg agtcttcagc agcag                               35

<210> SEQ ID NO 47
```

```
<211> LENGTH: 8
<212> TYPE: PRT
<213> ORGANISM: Artificial
<220> FEATURE:
<223> OTHER INFORMATION: synthetic peptide

<400> SEQUENCE: 47

Asp Tyr Lys Asp Asp Asp Asp Lys
1               5

<210> SEQ ID NO 48
<211> LENGTH: 7
<212> TYPE: PRT
<213> ORGANISM: Artificial
<220> FEATURE:
<223> OTHER INFORMATION: synthetic peptide

<400> SEQUENCE: 48

Ser Gly Gly Ser Gly Gly Ser
1               5

<210> SEQ ID NO 49
<211> LENGTH: 35
<212> TYPE: DNA
<213> ORGANISM: Artificial
<220> FEATURE:
<223> OTHER INFORMATION: primer

<400> SEQUENCE: 49
tgctctagag ctcttccaac ggtccgccgc cgggt                              35

<210> SEQ ID NO 50
<211> LENGTH: 21
<212> TYPE: DNA
<213> ORGANISM: artificial
<220> FEATURE:
<223> OTHER INFORMATION: primer

<400> SEQUENCE: 50
cctagggagc tcagcacgcg g                                            21

<210> SEQ ID NO 51
<211> LENGTH: 534
<212> TYPE: DNA
<213> ORGANISM: Artificial
<220> FEATURE:
<223> OTHER INFORMATION: synthetic construct
<220> FEATURE:
<221> NAME/KEY: CDS
<222> LOCATION: (1)..(534)

<400> SEQUENCE: 51 ggt ccg ccg ccg ggt ccg ccg cgt gtt tct ccg gac ccg cgt gct gag    48
Gly Pro Pro Pro Gly Pro Pro Arg Val Ser Pro Asp Pro Arg Ala Glu
1               5                   10                  15 ctc gat tct act gta ctg ctg act cgt tct ctg ctg gct gat act cgt    96
Leu Asp Ser Thr Val Leu Leu Thr Arg Ser Leu Leu Ala Asp Thr Arg
            20                  25                  30 cag ctg gct gca cag ctg cgt gat aaa ttt ccg gct gat ggt gac cat   144
Gln Leu Ala Ala Gln Leu Arg Asp Lys Phe Pro Ala Asp Gly Asp His
        35                  40                  45 aac ctg gat tct ctg ccg act ctg gca atg tct gca ggt gct ctg ggt   192
Asn Leu Asp Ser Leu Pro Thr Leu Ala Met Ser Ala Gly Ala Leu Gly
    50                  55                  60 gct ctg caa ctg ccg ggt gtt ctg act cgt ctg cgt gca gac ctg ctg   240
Ala Leu Gln Leu Pro Gly Val Leu Thr Arg Leu Arg Ala Asp Leu Leu
65                  70                  75                  80
```

```
tct tat ctg cgt cat gtt caa tgg ctg cgt cgt gca ggt ggt tct tct   288
Ser Tyr Leu Arg His Val Gln Trp Leu Arg Arg Ala Gly Gly Ser Ser
             85                  90                  95 ctg aaa act ctg gaa ccg gaa ctg ggt acc ctg caa gct cgt ctg gat   336
Leu Lys Thr Leu Glu Pro Glu Leu Gly Thr Leu Gln Ala Arg Leu Asp
        100                 105                 110 cgt ctg ctg cgt cgt ctg caa ctg atg tct cgt ctg gca ctg ccg       384
Arg Leu Leu Arg Arg Leu Gln Leu Met Ser Arg Leu Ala Leu Pro
            115                 120                 125 caa ccg ccg ccg gat ccg ccg gct ccg ccg ctg gct ccg ccg tct tct   432
Gln Pro Pro Pro Asp Pro Pro Ala Pro Pro Leu Ala Pro Pro Ser Ser
    130                 135                 140 gca tgg ggt ggt att cgt gca gct cac gct att ctg ggt ggt ctg cac   480
Ala Trp Gly Gly Ile Arg Ala Ala His Ala Ile Leu Gly Gly Leu His
145                 150                 155                 160 ctg act ctg gac tgg gca gtt cgt ggt ctg ctg ctt aag act cgt       528
Leu Thr Leu Asp Trp Ala Val Arg Gly Leu Leu Leu Lys Thr Arg
                165                 170                 175 ctg taa                                                           534
Leu
```

<210> SEQ ID NO 52
<211> LENGTH: 177
<212> TYPE: PRT
<213> ORGANISM: Artificial
<220> FEATURE:
<223> OTHER INFORMATION: Synthetic Construct

<400> SEQUENCE: 52

```
Gly Pro Pro Gly Pro Pro Arg Val Ser Pro Asp Pro Arg Ala Glu
1               5                   10                  15

Leu Asp Ser Thr Val Leu Leu Thr Arg Ser Leu Leu Ala Asp Thr Arg
                20                  25                  30

Gln Leu Ala Ala Gln Leu Arg Asp Lys Phe Pro Ala Asp Gly Asp His
            35                  40                  45

Asn Leu Asp Ser Leu Pro Thr Leu Ala Met Ser Ala Gly Ala Leu Gly
    50                  55                  60

Ala Leu Gln Leu Pro Gly Val Leu Thr Arg Leu Arg Ala Asp Leu Leu
65                  70                  75                  80

Ser Tyr Leu Arg His Val Gln Trp Leu Arg Arg Ala Gly Gly Ser Ser
                85                  90                  95

Leu Lys Thr Leu Glu Pro Glu Leu Gly Thr Leu Gln Ala Arg Leu Asp
            100                 105                 110

Arg Leu Leu Arg Arg Leu Gln Leu Met Ser Arg Leu Ala Leu Pro
        115                 120                 125

Gln Pro Pro Pro Asp Pro Pro Ala Pro Pro Leu Ala Pro Pro Ser Ser
    130                 135                 140

Ala Trp Gly Gly Ile Arg Ala Ala His Ala Ile Leu Gly Gly Leu His
145                 150                 155                 160

Leu Thr Leu Asp Trp Ala Val Arg Gly Leu Leu Leu Lys Thr Arg
                165                 170                 175

Leu
```